(12) United States Patent
Hannon, Jr.

(10) Patent No.: US 10,302,543 B2
(45) Date of Patent: May 28, 2019

(54) FULL IMMERSION PRESSURE-PULSE DECAY

(71) Applicant: The UAB Research Foundation, Birmingham, AL (US)

(72) Inventor: Michael J Hannon, Jr., Birmingham, AL (US)

(73) Assignee: The UAB Research Foundation, Birmingham, AL (US)

( * ) Notice: Subject to any disclaimer, the term of this patent is extended or adjusted under 35 U.S.C. 154(b) by 0 days.

(21) Appl. No.: 15/570,977

(22) PCT Filed: May 9, 2016

(86) PCT No.: PCT/US2016/031502
§ 371 (c)(1),
(2) Date: Oct. 31, 2017

(87) PCT Pub. No.: WO2016/179593
PCT Pub. Date: Nov. 10, 2016

(65) Prior Publication Data
US 2018/0348111 A1    Dec. 6, 2018

Related U.S. Application Data

(60) Provisional application No. 62/158,399, filed on May 7, 2015.

(51) Int. Cl.
| | |
|---|---|
| *G01N 15/08* | (2006.01) |
| *G01N 7/10* | (2006.01) |
| *G05B 13/04* | (2006.01) |
| *G01N 1/28* | (2006.01) |

(52) U.S. Cl.
CPC ........... *G01N 15/0806* (2013.01); *G01N 1/28* (2013.01); *G01N 7/10* (2013.01); *G01N 15/08* (2013.01); *G01N 15/088* (2013.01); *G05B 13/04* (2013.01)

(58) Field of Classification Search
None
See application file for complete search history.

(56) References Cited

U.S. PATENT DOCUMENTS

| | | | |
|---|---|---|---|
| 5,253,518 A | 10/1993 | Steigler | |
| 6,453,727 B1 | 9/2002 | Lenormand | |
| 7,051,808 B1 * | 5/2006 | Vinegar | B09C 1/02 166/250.01 |
| 2013/0054157 A1 | 2/2013 | Lasseux | |

(Continued)

OTHER PUBLICATIONS

Blaine R. Copenheaver, International Search Report and Written Opinion of the International Searching Authority, dated Aug. 12, 2016.

*Primary Examiner* — Andre J Allen
(74) *Attorney, Agent, or Firm* — Nicholas J. Landau; Bradley Arant Boult Cummings LLP

(57) ABSTRACT

The present disclosure provide a method and apparatus for pressure-pulse decay performed on whole cylindrical samples whose entire outer surface areas are eligible to receive the pulse. Using the methods and apparatus of the present disclosure, not only is the experimental time dramatically shortened, it also allows for simultaneous determination of local permeabilities parallel and perpendicular to their native bedding planes. Currently, there is no permeability-measurement technique to capable of doing so from a single sample from a single test.

42 Claims, 21 Drawing Sheets

(56) References Cited

U.S. PATENT DOCUMENTS

| | | |
|---|---|---|
| 2014/0069183 A1 | 3/2014 | Song et al. |
| 2016/0053612 A1* | 2/2016 | Proett ..................... E21B 49/10 166/264 |
| 2017/0205388 A1* | 7/2017 | Thomas ............... G01N 33/383 |
| 2018/0031732 A1* | 2/2018 | Mosse .................. G01V 99/005 |

* cited by examiner

† Changes in estimated values of $\widetilde{\lambda_x^2}$ limited to ensure $k_x < k_r$.

(a) $p_0 = 238.8$ psia, $p_p = 262.2$ psia (b) $p_0 = 476.8$ psia, $p_p = 519.4$ psia (c) $p_0 = 724.9$ psia, $p_p = 787.4$ psia (d) $p_0 = 898.9$ psia, $p_p = 976.5$ psia — Data   — Model (a) $p_0 = 253.5$ psia, $p_p = 277.0$ psia (b) $p_0 = 476.0$ psia, $p_p = 520.3$ psia (c) $p_0 = 727.1$ psia, $p_p = 796.8$ psia (d) $p_0 = 903.1$ psia, $p_p = 985.6$ psia —— Data —— Model (a) $p_0 = 247.0$ psia, $p_p = 271.9$ psia (b) $p_0 = 473.2$ psia, $p_p = 518.6$ psia (c) $p_0 = 751.3$ psia, $p_p = 824.0$ psia (d) $p_0 = 898.8$ psia, $p_p = 984.3$ psia —— Data —— Model (a) $p_0 = 249.3$ psia, $p_p = 274.9$ psia (b) $p_0 = 474.8$ psia, $p_p = 523.2$ psia (c) $p_0 = 699.9$ psia, $p_p = 769.9$ psia (d) $p_0 = 901.9$ psia, $p_p = 991.4$ psia —— Data  —— Model (a) UAB-1
(b) UAB-2
(c) UAB-3
(d) UAB-4

$$--- k_r = k_{\infty,r}\left(1 + \frac{b_r}{p_{ref}}\right) \quad --- k_x = k_{\infty,x}\left(1 + \frac{b_x}{p_{ref}}\right)$$

FULL IMMERSION PRESSURE-PULSE DECAY

CROSS-REFERENCE TO RELATED APPLICATIONS

This application is a national stage under 35 U.S.C. 371 of International Application PCT/US2016/031502, filed on May 9, 2016 (currently published). International Application PCT/US2016/031502 cites the priority of U.S. Provisional Patent Application No. 62/158,399, filed May 7, 2015.

BACKGROUND OF THE DISCLOSURE

To provide a greater understanding of critical parameters of ultra-tight geologic formations such as shales, the current experimental methodology on whole-core samples is in need of improvement. Core-scale measurements are considered the "ground truth" that interested parties, such as oil and gas companies and electric utility companies, use to predict migration of deep underground fluids (for example, oil, natural gas, $CO_2$ or brine) during extraction or injection operations. While prior art methods exists to make these assessments, interested parties often need to sacrifice measurement fidelity for a reasonable turnaround time, or vice versa. The present disclosure provides methods and apparatus to address this dilemma.

In recent years the industry has seen a dramatic shift in focus towards "tight" geologic formations such as shales, most notably as unconventional reservoirs for oil and gas exploration and as confining zones for carbon-sequestration operations. These formations have ultra-low permeabilities, meaning they are very difficult to penetrate. An accurate understanding a formation's permeability field is necessary to determine many operational parameters, such as but not limited to, ideal fracture spacing when drilling for oil and gas or to get accurate carbon-storage estimates. For example, a primary concern to the risks inherent in all carbon-sequestration operations is the prevention of upward migration of injected $CO_2$ from the geologic formation in which it is stored through its overlying caprock formations to the atmosphere or into underground sources of drinking water (USDW's). The purpose of the overlying caprock formations is to provide long-term sealing of the sequestered $CO_2$. Determining a safe amount of $CO_2$ to inject into a given reservoir calls for a comprehensive understanding of the integrity of its caprock. Part of this understanding involves accurate estimation of the permeability and porosity of the confining zone.

Making a quantitative permeability assessment always begins with the "ground truth" of core-scale measurements, but using conventional techniques to analyze ultra-low-permeability materials is notoriously onerous and time-consuming [1]. To overcome this limitation, experts across multiple disciplines have developed and refined a technique called "pressure-pulse decay" [2, 3], culminating in an experimental methodology referred to as the Gas Research Institute (GRI) method [4]. The GRI method is fast, but cannot be employed under in-situ conditions; nor is it repeatable across multiple laboratories [5, 6].

As previous investigations of pressure-pulse-decay measurements of fractured samples have demonstrated, one very influential indicator of experimental duration is the amount of sample surface area exposed to the pulse [7]. The GRI method took this concept to its logical conclusion by crushing the sample into small cuttings and analyzing a pulse decay applied to them [4]. However, since the size, shape and orientation of each cutting is arbitrary, defining a representative geometric domain for any model to compare against the resultant data is not feasible. Thus, the accuracy, repeatability and representativeness of the GRI model cannot be ensured, as reported throughout the technical literature [8, 9].

The present disclosure provides both methods and apparatus to simultaneously determine the porosity and permeabilities parallel and perpendicular to the native bedding planes using a single test on a single sample whose geometry is easily defined, such as for example a cylindrical core sample. Such methods and devices were not previously appreciated in the art.

DETAILED DESCRIPTION

The advent of permeametry and porosimetry methods using cylindrical porous samples by pressure-pulse decay arose from the need to more quickly characterize low-permeability geologic formations in the laboratory. However, due to time and leakage limitations, measuring samples having ultra-low permeabilities in the nanodarcy (nd) range or lower remains difficult using conventional pulse methods. This present disclosure provides a new method of pulse-decay measurements by fully immersing a sample in the permeant, thereby allowing entrance of the pressure pulse throughout the entire outer surface of the sample. Using the methods of the present disclosure, the testing times are decreased by more than an order of magnitude. An additional benefit to this technique is the ability to simultaneously measure the permeabilities parallel and perpendicular to the native bedding plane of the formation. Currently, there is no permeability-measurement technique capable of doing so from a single sample from a single test.

The methods of the present disclosure differ from the prior art techniques in several ways, including not limiting the pressure pulse to travel in a single direction. Rather, by extracting a sample from a formation oriented perpendicular to its bedding plane, one can readily interpret pressure-decay data under a scenario where all portions of its outer surface area are accessible to the incoming pulse. Under these conditions, one can reasonably assume migration of the permeant to be limited to only the axial and radial directions, and that the effective permeabilities in those directions remain uniform but distinct from one another. The pressure-pulse decay can then be compared against a numerical (or, in some cases, analytical) model to estimate the local principal permeabilities and porosity of the formation.

General Overview of the Method

The need for dependable experimental methodologies for the analysis of ultra-low permeability materials like shales has grown with industrial demand for understanding those lithologies. At present, interested parties are often forced to choose between time-consuming analyses having acceptable accuracy or rapid ones with limited accuracy and/or reproducibility (for example, the GRI method).

Figure 1:
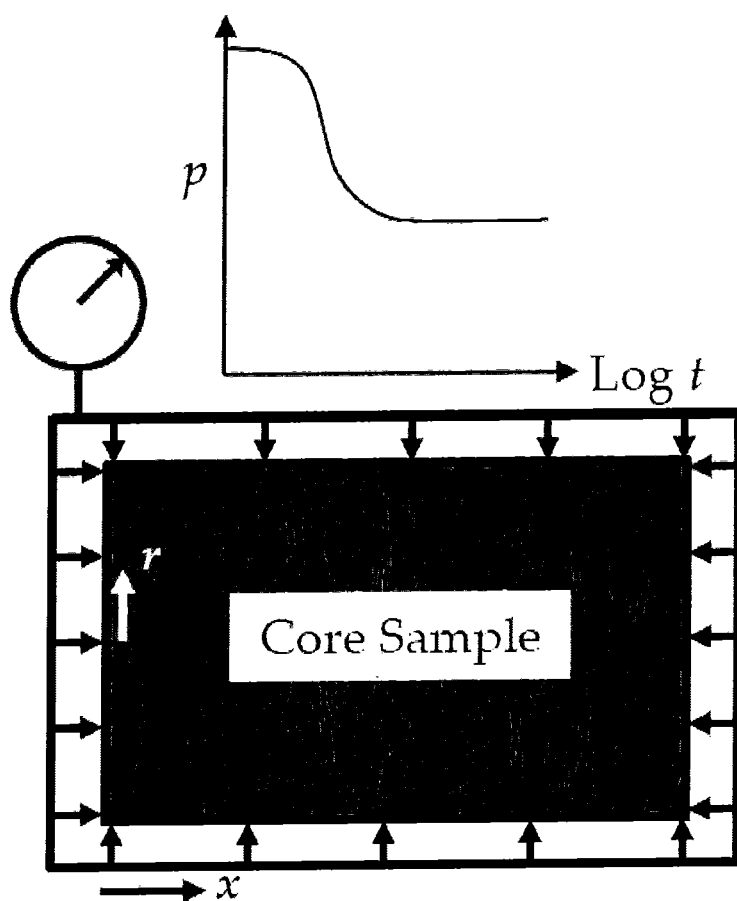
FIG. 1 shows a schematic of a fully immersed pressure-pulse decay experiment.

It is common knowledge among geophysicists that, at the field scale, the anisotropic permeability tensor has two principal axes: one oriented perpendicular to the bedding plane and one oriented parallel to it [10]. If a core sample is extracted normal to the bedding plane, one can reasonably assume the principal axes of permeability to be along the axial and radial directions. This is particularly true in the presence of uniform radial confining stress, which is the only state achievable with current experimental apparatuses. By pressurizing a permeant surrounding the outer surface area of the sample and applying a step increase in pressure to the entire outer surface of the sample as shown in FIG. 1, the resultant pressure gradient is also oriented only in the axial and radial directions, thereby inducing flow through the sample in only those directions.

The present disclosure provides a full immersion pressure-pulse decay method that is capable of analyzing samples in a turnaround time similar to that of the GRI technique. It does so by applying a step change in pressure on the entire outer surface area of a cylindrical sample, as shown in FIG. 1.

The methods of the present disclosure comprise the analysis of the full immersion pressure-pulse decay performed on a sample. In a general overview of the method, the sample is placed in a reservoir and the sample and the reservoir are equilibrated to an initial equilibrated pressure $p_0$ with a permeant (for example, a gas or a liquid). Next a pressure pulse is applied to the reservoir and the sample, wherein the pressure pulse increases the pressure in the reservoir to a pressure greater than the equilibrated pressure $p_0$. The data obtained is pressure change over time, with the pressure gradually decreasing from the pulsed pressure over time as the permeant enters the sample, thereby decreasing the pressure measured in the reservoir. The pressure pulse, as described herein, is generally 5% to 10% of the equilibrated pressure $p_0$. A wide range of values may be chose for the equilibrated pressure $p_0$. However, the equilibrated pressure $p_0$ is generally selected to be high enough so that the pressure pulse provides changes in data that can be readily measured (for example, over 250 psi).

A variety of samples may be used in conjunction with the methods disclosed herein. In certain embodiments, the sample is one whose geometry is easily defined, such as but not limited to a cylindrical sample. In certain embodiments, the sample is a core sample. In certain embodiments, the sample is a cylindrical core sample. In certain embodiments, the sample is a cylindrical core sample. In certain embodiments, the sample is a core sample, the core sample having a geometry that is easily defined. In certain embodiments, the sample is not a fractured sample. In certain embodiments, the sample is not a crushed sample. Regardless of the nature of the sample, in certain embodiments the entire outer surface of the sample receives the pressure pulse as described herein whose entire outer surface areas are eligible to receive the pulse.

The permeant may be any liquid or gas as is known in the art. In one embodiment, the permeant is a liquid, such as water or brine. In another embodiment, the permeant is a gas, such as $N_2$ or He. In certain embodiments, a gaseous permeant is used as liquid permeants have a higher viscosity. In certain embodiments, the permeant is a gaseous permeant and the sample is one whose geometry is easily defined, such as but not limited to a cylindrical sample, a core sample or a cylindrical core sample and in certain embodiments, the sample is not a fractured sample or a crushed sample. In certain embodiments, the permeant is $N_2$ or He and the sample is one whose geometry is easily defined, such as but not limited to a cylindrical sample, a core sample or a cylindrical core sample and in certain embodiments, the sample is not a fractured sample or a crushed sample.

Essentially any pressure may be used as the equilibrium pressure, depending on the ability of the various components of the apparatus to withstand such pressures. In one embodiment, the equilibrium pressure is from about 500 to 3000 psia. In another embodiment, the equilibrium pressure is greater than 3000 psia and less than 10,000 psia. In another embodiment, the equilibrium pressure is from about 750 to 1250 psia. In another embodiment, the equilibrium pressure is from about 900 to 1100 psia. In another embodiment, the equilibrium pressure is about 1000 psia or 950 psia.

The pressure pulse may be a pulse in pressure as desired, provided that the pressure pulse may be detected. In one embodiment, a small pressure pulse (as compared to the equilibrium pressure) is applied as is known in the art for non-full immersion pressure pulse decay. In one embodiment, the pressure pulse is from about 2% to 15% of the equilibrium pressure. In another embodiment, the pressure pulse is from about 4% to 13% of the equilibrium pressure. In another embodiment, the pressure pulse is from about 5% to 10% of the equilibrium pressure. A pressure pulse is then applied instantaneously or substantially instantaneously along the entire outer surface area of the sample. As used herein, the term "substantially instantaneously" means the pressure pulse is applied on the order of tens of milliseconds (for example, 10 milliseconds) or faster.

Through the use of the methods of the present disclosure not only are the experimental times dramatically reduced, it also allows for simultaneous determination of local permeabilities parallel and perpendicular to their native bedding planes; the porosity of the sample may also be simultaneously determined from the sample concurrently with the determination of the local permeabilities parallel and perpendicular to their native bedding planes. Therefore, the present disclosure provides a method for simultaneously determining a permeability in the radial direction and a permeability in the axial direction and a porosity of a sample. For clarity, using the methods of the present disclosure, the information required to determine the permeability in the radial direction, the permeability in the axial direction and the porosity of the sample are generated. However, the methods disclosed to not require the values for the permeability in the radial direction, the permeability in the axial direction and the porosity to be determined in every case. For example, the permeability in the radial direction and the permeability in the axial direction may be determined and reported, while the porosity value is not determined or is determined and not reported. Likewise, the methods of the present disclosure do not require both the radial and axial permeabilities to be reported. For example, the permeability in the radial direction and the permeability in the axial direction may be determined, but only the permeability in the radial or axial direction reported. In a one embodiment, the porosity, the radial permeability and the axial permeability are determined and reported. Currently, there is no permeability-measurement technique to determine these parameters from a single sample using a single test.

By inverting this model, the porosity and principal permeabilities can be estimated simultaneously. The experimental procedure includes, but is not limited to, the design schema described in the embodiments below. Note that, although not indicated, the methodologies described herein can also incorporate a tri-axial confining stress.

General Overview of the Analysis of Data

Figure 2:
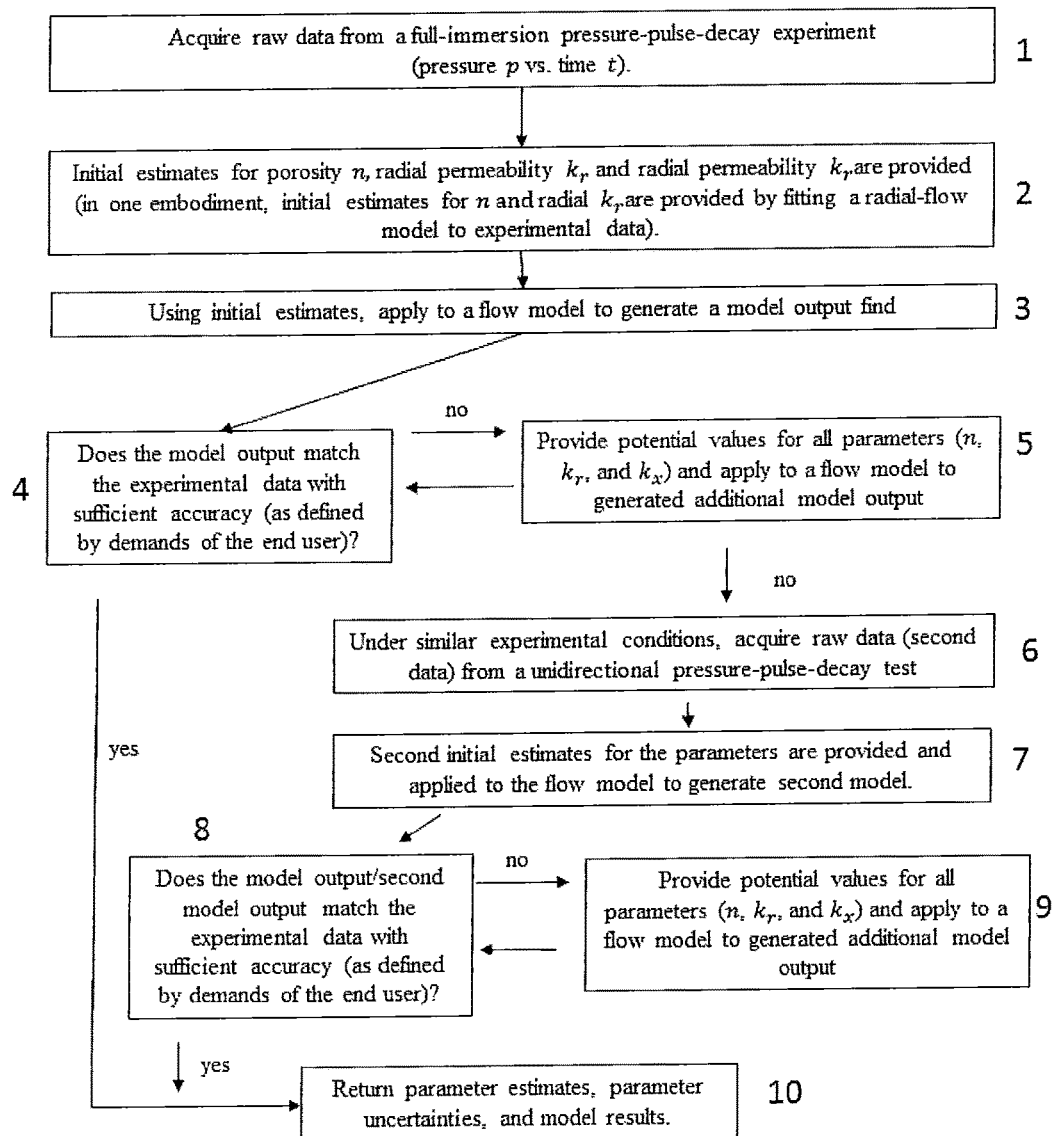
FIG. 2 shows a flowchart illustrating basic steps of the method for determining radial and axial permeability.

The general steps for the conduct of the methods and the analysis of data are provided in FIG. 2. In Box 1 raw data is acquired from an experimental system (for example, a system as described in Example 1) wherein a sample is subject to a full immersion pressure-pulse decay experiment. Details on the experimental methodology are provided herein. The data obtained is pressure change over time, with the pressure gradually decreasing over time as the permeant enters the sample, thereby decreasing the pressure measured in the reservoir. The rate at which the pressure drops is dependent on the axial and radial permeabilities.

Initial estimates for the porosity (n), radial permeability ($k_r$) and the axial permeability ($k_x$) are then provided (Box 2). In certain embodiments, the initial estimates for the porosity (n) and radial permeability ($k_r$) are provided by fitting the experimental data obtained to a radial flow model as is known in the art and as described here. In other embodiments, educated guesses about the initial estimates can be provided. In certain embodiments, the initial estimate for the axial permeability ($k_r$) is small (for example 0.5% to 2.0% of the radial permeability, $k_r$) as the axial permeability is generally less than the radial permeability in many sample types (for example, shales).

The initial estimates, however obtained, are used with a flow model to provide a model output (Box 3). The model output is compared to the experimental data (Box 4). If the model output and the experimental data provide an acceptable fit, then the initial estimates for the porosity, radial permeability and the axial permeability are identified as the values for the porosity, radial permeability and the axial permeability (Box 8). If, as will be the case in most circumstances, the initial estimates for the porosity, radial permeability and the axial permeability do not result in acceptable fit of the model output to the experimental data, the initial estimates of the porosity, radial permeability and the axial permeability are selectively varied using conventional parameter-estimation techniques (these values are referred to as potential values) and input into the flow model to generate additional model output which is then compared to the experimental data (Box 5). The process is repeated to identify a combination of all parameters (n, $k_r$, and $k_x$) that produces model output that best fits the experimental data, optionally along with uncertainty estimates for each parameter (i.e., until the model output results in an acceptable fit to the experimental data) (Box 4). In this case, the potential values for the porosity, radial permeability and the axial permeability that provide a model output with an acceptable fit to the experimental data are identified as the values for the porosity, radial permeability and the axial permeability (Box 10).

As used herein, the term "acceptable fit" and similar terms refers to a model output that meets the criteria defined by its application, often determined by the end user of the analyses. In certain embodiments, the model output includes uncertainty estimates for the radial permeability, the axial permeability and the porosity and the uncertainty estimate is used to determine if the model output provides the acceptable fit to the data.

In certain circumstances, using the methods above, the flow model may not yield output data that is an acceptable fit to the experimental data. In such circumstances, the method may further comprise obtaining under the same or similar experimental conditions additional experimental data (referred to as a second data) by applying the pressure pulse to the axial face or the radial surface of the sample only (and not the entire outer surface of the sample) (Box 6).

Second initial estimates for the radial permeability or the axial permeability and the porosity are then provided. In certain embodiments, the second initial estimates for the radial permeability or the axial permeability and the porosity are provided from the estimates obtained from the full immersion pressure-pulse decay method above (Box 7). In other embodiments, educated guesses about the second initial estimates can be provided. The second initial estimates, however obtained, are used with the same or similar flow model as used initially to provide a second model output along with the first estimates. The model output and second model output are compared to the experimental data and the second experimental data (Box 8). If the model output and second model output provide an acceptable fit, the potential values/second potential values for the porosity, radial permeability and the axial permeability that provide a model output with an acceptable fit to the experimental data and the second experimental data are identified as the values for the porosity, radial permeability and the axial permeability (Box 10). If not, the initial estimates of the porosity, radial permeability and the axial permeability and the second initial estimates of the radial permeability or the axial permeability and the porosity are selectively varied using conventional parameter-estimation techniques to provide potential values and second potential values, which are then each input into the flow model to generate model output and second model output, respectively, which are then compared to the experimental data and the second experimental data (Box 9). The process is repeated until the model output and second model output results in potential values for the porosity, radial permeability and the axial permeability that are an acceptable fit to the experimental data and the second model output results in potential values for the radial permeability or the axial permeability and porosity that are an acceptable fit to the second experimental data. In this case, the potential values/second potential values for the porosity, radial permeability and the axial permeability that provide model output/second model output that are an acceptable fit for the data and the second data are identified as the values for the porosity, radial permeability and the axial permeability (Box 10).

The multidirectional, axi-symmetric flow model required to analyze data from this approach does not lend itself as easily to analytical solutions, but can be approximated using numerical simulations, such as the one outlined herein. Most models assume that the samples under investigation are composed of an isotropic fabric. Given the strong anisotropic nature of layered media, such as, but not limited to, shales or mudrocks, this assumption is seldom applicable to materials of interest. The full-immersion pressure-pulse decay relaxes this assumption and replaces it with a model more representative of the materials of interest in the field.

As discussed above, pressurizing a permeant surrounding the entire outer surface area of this sample and applying a step increase in pressure to the entire outer surface of the sample (see FIG. 1), results in a pressure gradient that is also oriented only in the axial and radial directions, thereby inducing flow through the sample in only those directions. These assumptions simplify the governing equations of motion to produce a reducible model to compare against experimental data.

The following provides an example of the steps to obtain values of radial and axial permeabilities and porosity of a sample using a gaseous permeant. Assuming the permeant travels along axisymmetric flow paths described above, the governing equation of motion, in non-dimensional form, is provided by Eq. 1.

$$\frac{\partial p_D^*}{\partial t_{D,R}^*} = \frac{\mu c}{(\mu c)_{ref}} \frac{\partial p_D^*}{\partial t_{D,R}} = \frac{1}{r_D}\frac{\partial p_D^*}{\partial r_D} + \frac{\partial^2 p_D^*}{\partial r_D^2} + \lambda_x^2 \frac{\partial^2 p_D^2}{\partial x_D^2} \quad (1)$$

Since its solution will be approximated numerically, it is written in both the standard time domain t (for simpler comparison to experimental data) and the pseudo-time domain t* (for comparison to analytical models). The time constant $\tau_R$ (defined in Eq. 2) normalizing the temporal coordinate is based on the sample radius R and permeability in the radial direction $k_r$. This was chosen in light of the fact that, due to higher radial permeability and relatively faster radial infiltration, flow is expected to travel predominantly in the radial direction.

$$\tau_R \equiv \frac{n(\mu c)_{ref} R^2}{k_r} \quad (2)$$

Due to symmetry, the axial coordinate x is normalized in this scenario by half the length of the sample (i.e., $x_D=2x/L$). Also, a new dimensionless parameter $\lambda_x^2$, defined by Eq. 3, contains the ratio of axial (i.e., perpendicular to bedding) to radial (parallel to bedding) permeability.

$$\lambda_x^2 \equiv \frac{k_r}{k_r}\left(\frac{D}{L}\right)^2 \quad (3)$$

Equation 4 defines the initial pressure disturbance in the reservoir space ($r_D=1$, $x_D=0$) applied to the initial equilibrium pressure state within the pore space ($0 \leq r_D < 1$, $0 < x_D \leq 1$).

$$p_D^*(r_D, x_D, t_{D,R} = t_{D,R}^* = 0) = \begin{cases} 0, & 0 \leq r_D < 1, 0 < x_D \leq 1 \\ 1, & r_D = 1, x_D = 0 \end{cases} \quad (4)$$

The boundary conditions describe the absence of flow in the inner boundaries (axis and center plane) of the sample (Eq. 5) and provide a material balance between the reservoir space and the mass flow through the outer surface of the sample (Eq. 6).

$$\frac{\partial p_D^*}{\partial r_D}\bigg|_{r_D=0} = \frac{\partial p_D^*}{\partial x_D}\bigg|_{x_D=1} = 0 \quad (5)$$

$$\frac{\gamma}{2}\frac{\partial p_D^*}{\partial t_{D,R}^*}\bigg|_{\substack{r_D=1 \\ x_D=0}} = \quad (6)$$

$$\frac{\gamma}{2}\frac{\mu c}{(\mu c)_{ref}}\frac{\partial p_D^*}{\partial t_{D,R}}\bigg|_{\substack{r_D=1 \\ x_D=0}} = \lambda_x^2 \int_0^1 \frac{\partial p_D^*}{\partial x_D}\bigg|_{x_D=0} r_D dr_D - \int_0^1 \frac{\partial p_D^*}{\partial r_D}\bigg|_{r_D=1} dx_D$$

Figure 4:
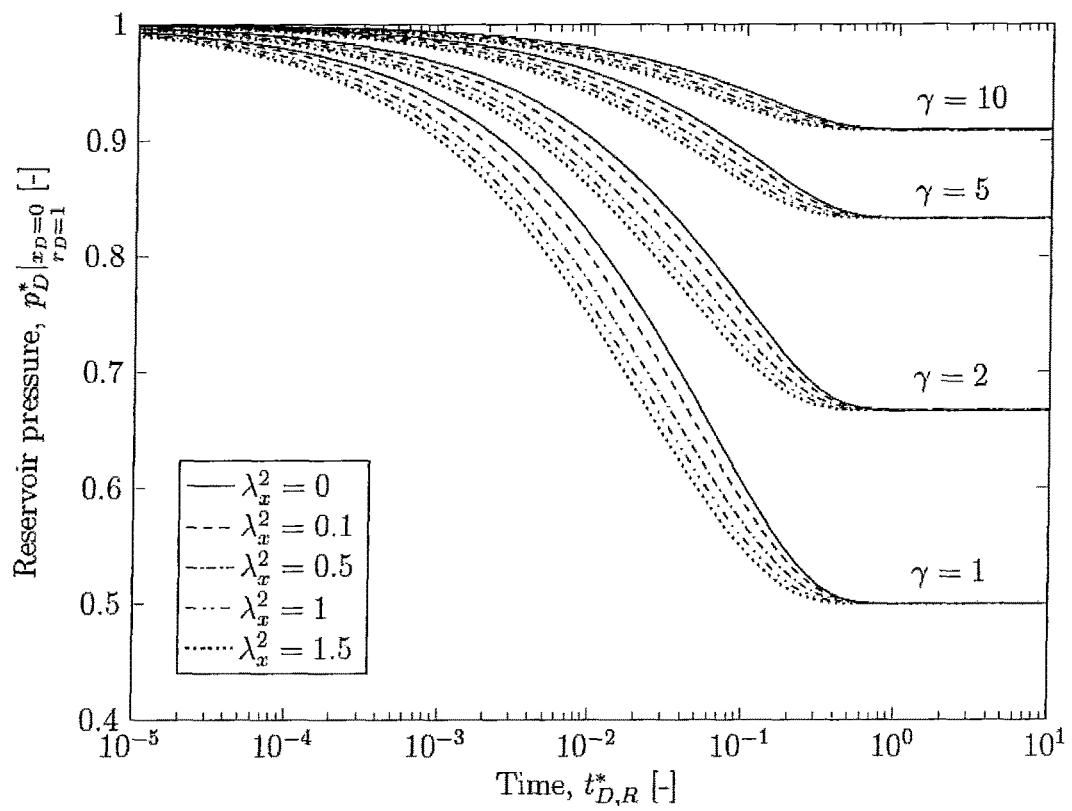
FIG. 4 shows the dependence of reservoir pressure on time during an axi-symmetric fully-immersed pressure-pulse decay with varying permeability ratios $\lambda_x^2$ and ratios of reservoir volume to pore volume $\gamma$.

A numerical discretization scheme was employed to determine an approximate solution of Eqs. 1 to 6. Using this solution, the dependence of reservoir pressure ($p_D^*|_{r_D=1,x_D=0}$) on time for various values of $\lambda_x^2$ and $\gamma$ is shown in FIG. 4. The cases of $\lambda_x^2=0$ (shown in solid black lines) are produced using a previously derived analytical model for the radial flow problem, which demonstrates good agreement with the numerical solution for the axi-symmetric model. In all cases, the ratio of reservoir volume to pore volume, $\gamma$, predominantly affects the final equilibrium pressure of the test, and the normalized permeability ratio $\lambda_x^2$ determines the deviation of the pressure-response curve from the radial-flow solution. The effect of $\lambda_x^2$ on the flow model is investigated more thoroughly herein.

Figure 3:
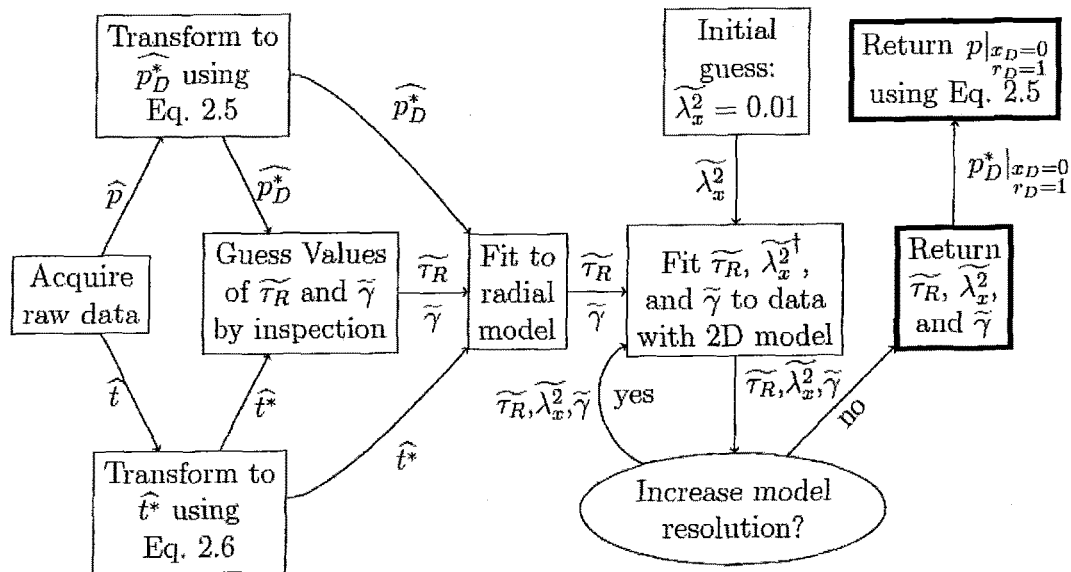
FIG. 3 shows a flowchart illustrating the steps in the parameter-estimation algorithm for analysis of data from a single experiment. Analogous schemes are employed for simultaneous analysis of multiple tests of the same sample accounting for Klinkenberg effects at different reference pressures.

The flow diagram provided in FIG. 3 outlines the algorithm employed to determine the reservoir to pore volume ratio γ, the radial flow time constant $\tau_R$, and the normalized axial to radial permeability ratio $\lambda_x^2$, based on data from a single experiment. In most materials investigated using this technique, it is likely for the flow to occur predominantly in the radial direction. This is due both to the higher expected radial permeability ($k_r > k_x$) as well as the higher efficiency for radial flow to infiltrate a standard-sized cylindrical sample. As a result, the analytical and computationally efficient radial-flow model provides useful initial estimates of the parameters. Final parameter estimates are then determined by the degree to which the experimental data deviate from the radial-flow model. Limitations are also placed on parameter estimates to ensure $k_r > k_x$ while approaching the solution.

Measured quantities are denoted with the superscript A, and parameter estimates are denoted with the superscript ~. The raw pressure traces are transformed to the dimensionless pseudo-pressure and pseudo-time domains to provide the initial estimates of $\widetilde{\tau_R}, \tilde{\gamma}$, and $\widetilde{p_p^*}$ using the analytical radial flow model. From this point, while pressure data remain as normalized pseudo-pressures, the numerical model outputs values of $p_D^*$ in the standard temporal domain t. Using a sufficiently small value of $\lambda_x^2$ as an initial guess, along with the initial estimates of the remaining parameters, updated estimates of all parameters are determined by fitting the model at a coarse spatial resolution to the data. Details on the weighted-least-squares curve-fitting scheme employed using both the numerical and analytical models is provided herein. Estimates are updated with increasing spatial resolution in the numerical model until acquiring a fit at a sufficiently high spatial resolution, resulting in the final estimates of parameters $\widetilde{\tau_R}$, $\widetilde{\lambda_x^2}$, $\gamma$, and $\widetilde{p_p^*}$.

Figure 5A:
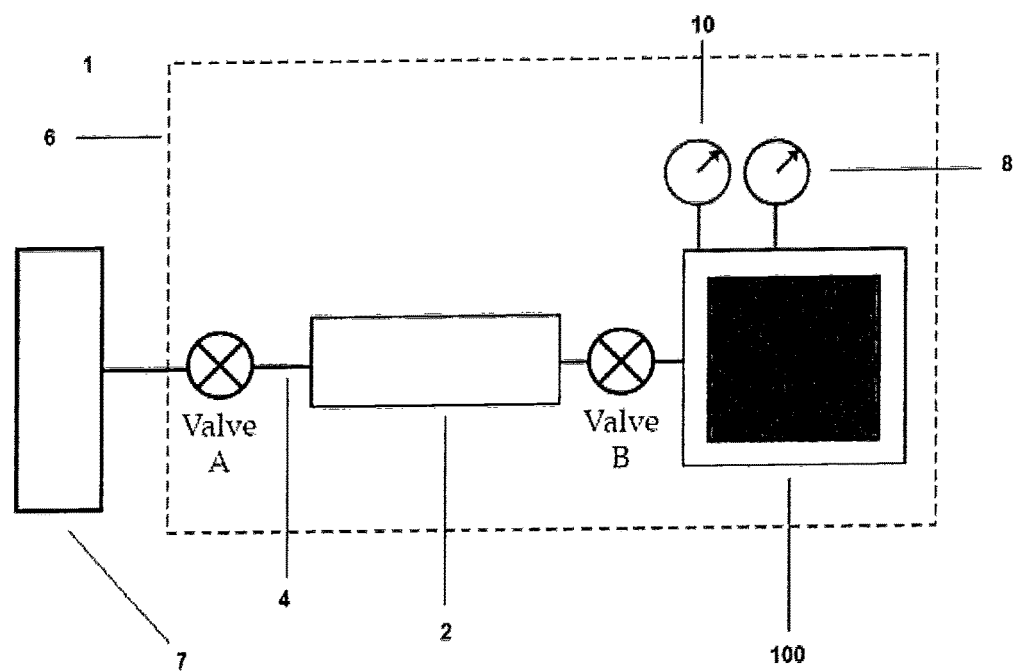
FIG. 5A shows one embodiment of an exemplary test apparatus for use in the methods of the present disclosure.
Figure 5B:
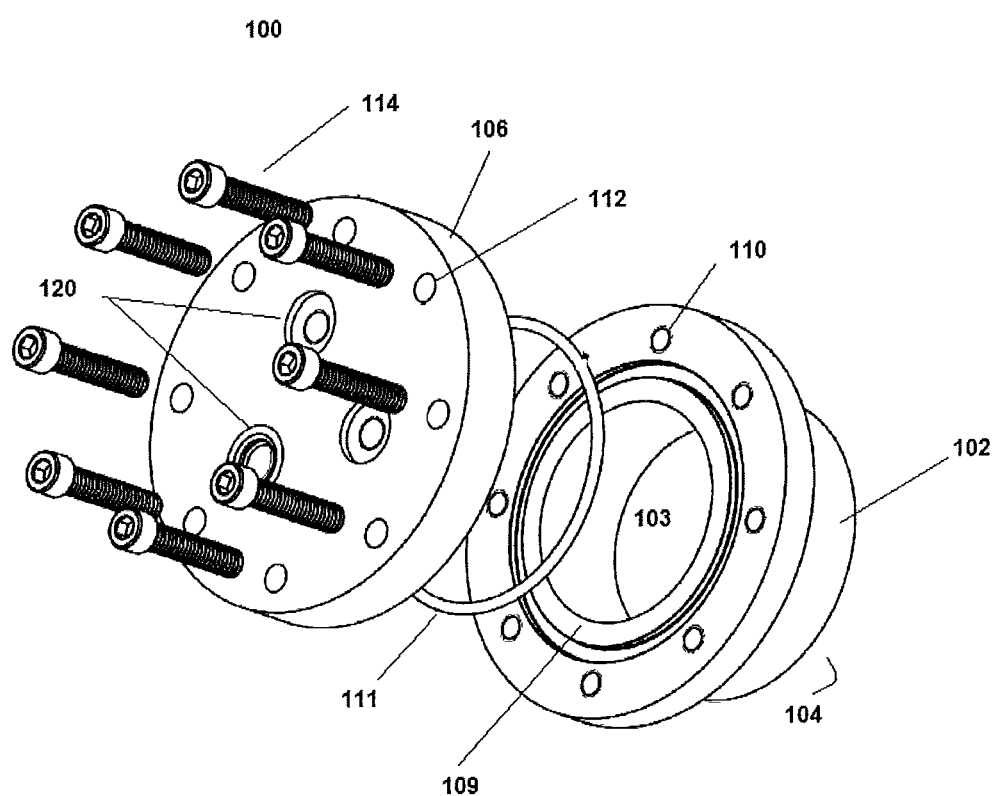
FIG. 5B shows one embodiment of an exemplary design of a test cell 100 for use in the methods of the present disclosure.

FIGS. 5A and 5B gives a schematic for the simplest application of this design of experiment. A sample is placed in an apparatus and pressurized with permeant to an elevated level. Through the equations described herein, the disclosed analysis may be applied to any thermodynamic state. Before the pressure pulse is applied, the reservoir (also referred to as the test cell) holding the sample is pressurized to an equilibrium pressure. Essentially any pressure may be used as the equilibrium pressure, depending on the ability of the various components of the apparatus to withstand such pressures. In one embodiment, the equilibrium pressure is from about 500 to 3000 psia. In one embodiment, the equilibrium pressure is greater than 3,000 psia but less than 10,000 psia. In another embodiment, the equilibrium pressure is about 750 to 1250 psia. In another embodiment, the equilibrium pressure is from about 900 to 1100 psia. In another embodiment, the equilibrium pressure is about 1000 psia or 950 psia. A pressure pulse is then applied instantaneously or substantially instantaneously along the entire outer surface area of the sample. In one embodiment, a small pressure pulse (as compared to the equilibrium pressure) is applied as is known in the art for non-full immersion pressure pulse decay. In one embodiment, the pressure pulse is from about 2% to 15% of the equilibrium pressure. In another embodiment, the pressure pulse is from about 4% to 13% of the equilibrium pressure. In another embodiment, the pressure pulse is from about 5% to 10% of the equilibrium pressure. In a specific embodiment, the apparatus is pressurized to 950 psia and the pressure pulse is 50 psia. At a rate and manner largely dependent on the two principal permeabilities (the radial and axial permeabilities), the pulse eventually reaches a new equilibrium, largely dependent on the porosity of the sample.

A more direct approach to permeability measurement form a single pressure trace would be to isolate flow to a single direction. The standard pressure-pulse-decay method already does this by isolating flow in the axial direction. But one could also limit flow to the radial direction using the schematic shown in FIG. 6B. This approach uses a seal placed on both ends of the sample. The complexity of the resultant flow model reduces to an analytical solution. For a standard 1 inch diameter, 1 inch long core size, such a test would still take noticeably less time to complete than the conventional pressure-pulse decay. The seal may be composed of any material that is known in the art. In one embodiment, the seal is a combination of rubber and a metal foil.

As permeabilities perpendicular to bedding plane of materials of interest (such as but not limited to, shales and mudstones) are typically much lower than those parallel to it, the pulse-decay behavior will be less sensitive to the former than the latter, resulting in larger confidence intervals for the axial permeability estimate. As small changes in the horizontal permeabilities may compensate for large ones in the axial permeabilities, this calls into question the uniqueness of the solution one obtains by applying the multi-permeability model to a single pressure trace. However, one can apply the purely radial-flow model to the pressure-decay data from a fully-immersed scenario to create an informed initial guess to the overall parameter-estimation procedure. Doing so accurately resolves all parameters of interest (i.e. principal permeabilities and porosity) over a wide range of anticipated outcomes (see for example, FIGS. 12 and 15).

Therefore, in one embodiment, the present disclosure provides for application of full immersion pressure-pulse-decays methods in the following flow scenarios.

First, a pulse applied around the circumferential portion of a cylindrical sample, inducing purely radial flow and providing a dramatic (i.e. at least an order of magnitude) decrease in experimental time. An analytical model was developed for this scenario.

Second a pulse applied to the entire outer surface area of a cylindrical sample cut perpendicular to formation bedding plane, inducing simultaneous radial and axial flow and providing an even faster test that also has the ability to simultaneously determine permeability parallel and perpendicular to bedding plane from a single test on a single sample. A numerical model was developed for this scenario. Ascertaining both permeabilities in the scenario described above is only possible with a sufficiently accurate initial guess in the parameter-estimation scheme. This guess is provided by applying the flow model described the paragraph above to the experimental data.

In one embodiment, the present disclosure provides a method for simultaneously characterizing a radial permeability, axial permeability, and a porosity, of a sample whose geometry is easily defined, the method comprising the steps of: (i) placing the sample in a sealed reservoir containing a permeant such that the entire outer surface of the sample is exposed to the permeant; (ii) equilibrating an internal pore pressure of the sample and a pressure of the reservoir to reach an equilibrated pressure $p_0$; (iii) applying a pressure pulse to the reservoir and the entire outer surface area of the sample, wherein the pressure pulse increases the pressure in the reservoir to a pressure greater than the equilibrated pressure $p_0$; (iv) obtaining data representative of a pressure decay over time in the reservoir after application of the pressure pulse; (v) inputting an initial estimate for the radial permeability, the axial permeability and the porosity based on the data into a flow model to generate a model output; (vi) providing potential values of the radial permeability, the axial permeability and the porosity based on the data until the model output provides an acceptable fit to the data; and (vii) using the potential values of the radial permeability, the axial permeability, and the porosity, that provide an acceptable fit to the data as the values for the radial permeability, the axial permeability, and the porosity.

In certain embodiments, the method further comprises: (i) obtaining under the same or similar experimental conditions a second data set by applying the pressure pulse to the axial face or the radial surface of the sample; (ii) inputting a second initial estimate for the radial permeability or the axial permeability and the porosity into the flow model to generate a second model output; (iii) providing potential values of the radial permeability, the axial permeability and the porosity until the model output provides an acceptable fit to the data and providing potential values for the radial permeability or the axial permeability and the porosity until the second model output provides an acceptable fit to the second data; and (iv) using the potential values of the radial permeability, the axial permeability, and the porosity, that provide an acceptable fit to the data and the second data as the values for the radial permeability, the axial permeability, and optionally the porosity.

In another embodiment, the present disclosure provides a method for simultaneously characterizing a radial permeability, axial permeability, and a porosity, of a cylindrical sample, the method comprising the steps of: (i) placing the sample in a sealed reservoir containing a permeant such that the entire outer surface of the sample is exposed to the permeant; (ii) equilibrating an internal pore pressure of the sample and a pressure of the reservoir to reach an equilibrated pressure $p_0$; (iii) applying a pressure pulse to the reservoir and the entire outer surface area of the sample, wherein the pressure pulse increases the pressure in the reservoir to a pressure greater than the equilibrated pressure $p_0$; (iv) obtaining data representative of a pressure decay over time in the reservoir after application of the pressure pulse; (v) inputting a series of potential values for each of a plurality of parameters based on the data into an expression to produce a model output until the model output provides an acceptable fit to the data; (vi) determining the value for each of the plurality of parameters using the potential values of each of the plurality of parameters that provide an acceptable fit between the model output and the data; and (vii) determining the radial permeability, the axial permeability and the porosity from the values.

In certain embodiments, the expression is a governing flow equation. In certain embodiment, the governing flow equation is:

$$\frac{\partial p_D^*}{\partial t_{D,R}^*} = \frac{\mu c}{(\mu c)_{ref}} \frac{\partial p_D^*}{\partial t_{D,R}} = \frac{1}{r_D} \frac{\partial p_D^*}{\partial r_D} + \frac{\partial^2 p_D^*}{\partial r_D^2} + \lambda_x^2 \frac{\partial^2 p_D^*}{\partial x_D^2},$$

wherein $$\tau_R \equiv \frac{n(\mu c)_{ref} R^2}{k_r} \text{ and } \lambda_x^2 \equiv \frac{k_r}{k_r}\left(\frac{D}{L}\right)^2.$$

In certain embodiments, the method further comprises determining a second permeability in the radial direction or a second permeability in the axial direction of the sample, the method comprising the steps of: (i) obtaining under the same or similar experimental conditions a second data representative of a pressure decay over time in the reservoir after application of the pressure pulse; (ii) inputting the series of potential values based on the data and a series of second potential values based on the second data for each of the plurality of parameters into the expression to produce the model output and a second model output until the model output and second model output provides an acceptable fit to the data and the second data; (iii) determining a value for each of the plurality of parameters using the potential values and second potential values of each of the plurality of parameters that provide an acceptable fit between the model output and the data and the second model output and the second data; and (iv) determining the permeability in the radial direction, the permeability in the axial direction, and optionally the porosity, from the values.

EXAMPLES

Example 1—Exemplary Test Apparatus

As with many conventional pressure-pulse-decay strategies, accurate parameter estimates require experiments that are relatively leak-free and isothermal as well as methods to account for non-ideal conditions. Beyond the standards of conventional methods, the full-immersion technique also requires highly accurate data, with standard deviations preferably approaching $1 \times 10^{-4}$, or roughly 0.01% of the initial pressure range ($p_p - p_0$) of the experiment. The experimental design to address the former issue and the data-acquisition algorithm to address the latter are discussed. FIG. 5A shows an exemplary test apparatus for use in the methods of the present disclosure. Apparatus 1 comprises a reference reservoir 2 of known volume in fluid communication through Valve A and supply line 4 to a supply of permeant (for example a gas) and in fluid communication with test cell 100 through valve B and supply line 4. The reference reservoir 2 and test cell 100, along with supply line 4 and valves A and B are placed in a temperature-controlled incubator 6. The test cell 100 comprises a pressure sensor (10) and optionally other sensors for monitoring the conditions of the test cell, such as a temperature sensor (8). Valves A and B allow the reference reservoir 2 and the test cell 100 to be isolated from each other and the source of permeant 7. The supply line 4 provides a closed fluid path between the source of the permeant, the reference reservoir and the test cell. The source of the permeant may also comprise a pressure regulator that releases the permeant into the system at constant pressure. The pressure sensor 10 and optionally the other sensors provide a fast response time on the order of tens of milliseconds or less to obtain the data (such response times are available commercially in a wide range of pressure sensors). The apparatus may contain additional sensors (such as, but not limited to, pressure sensors and temperature sensors) at various locations to monitor the conditions of the system.

In operation, the reference reservoir 2, the dead space in test cell 100 and the pore volume of the sample are brought to an equilibrium pressure. After such equilibrium pressure is achieved, valve B is closed and the reference volume is pressurized to a desired pressure to provide a pressure pulse as discussed herein. A test is initiated by quickly opening Valve B (which may be under electronic control), which is deemed to occur instantaneously or substantially instantaneously. The rapid pressure change in the test cell 100 also introduces temperature anomalies due to the Joule-Thomson effect and adiabatic expansion, but the temperature of the test cell typically remain within 0.1-0.2° C. of the equilibrated system temperature and quickly returns to the original temperature. Throughout the duration of a test, system temperatures are maintained by placing the system in an incubator capable of maintaining temperatures within ±0.5° C. or less.

The components of the system, for example, valves A and B and pressure sensor 10 (as well as any additional components) may be in electrical communication with a data processing system. The data processing system is capable of controlling the components of the system as well as recording data and analyzing the data.

FIG. 5B shows an exemplary design of a test cell 100 for use in the methods of the present disclosure. The test cell comprises a reservoir 102 for containing a sample, the reservoir 102 having an interior space 103 bounded by a bottom 104, a side wall 105 and a removable top portion 106 secured to reservoir 102. The reservoir is adapted to removable receive the top portion 106 such that a pressure seal is created between the reservoir 102 and the top portion 106. In the example illustrated, reservoir 102 has a flange portion 108 with threaded receivers 110 to securely and removable receive bolts 114, while top portion 106 has aligned openings 112 to allow the bolts 114 to engage the threaded receivers 110. The flange portion forms a seat 109 to receive gasket 111, which provides the pressure seal when the top portion 106 is secured to the reservoir 102. The reservoir may optionally contain additional openings, designated 120 for the attachment of instruments to monitor the experiment, such as but not limited to pressure sensors, temperature sensors and the like.

The test cell is preferably pressure sealed and capable of maintaining such seal under pressure. Such seals are provided as is known in the art, such as through the use of gaskets, O-rings, sealants and the like.

While the test cell 100 is shown to be circular in this embodiment, other shapes for the test cell 100 are possible. In certain embodiments, reservoir 102 is configured to be only slightly larger than the sample received. In certain embodiments, the reservoir 102 is configured such that the dead space between the sample and the side wall 106 and/or top portion is less than 1 inch, 2 inches, 3 inches, 4 inches or 5 inches.

Figure 6A:
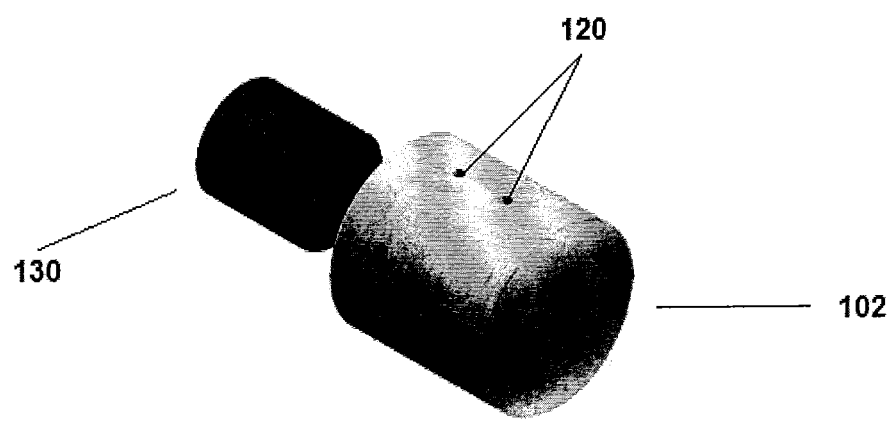
FIG. 6A shows an embodiment of the test cell involving a single pressure transducer allowing flow in both axial and radial directions. The two holes along the curved surface of the apparatus allow access for a pressure sensor and connection with the fluid supply.
Figure 6B:
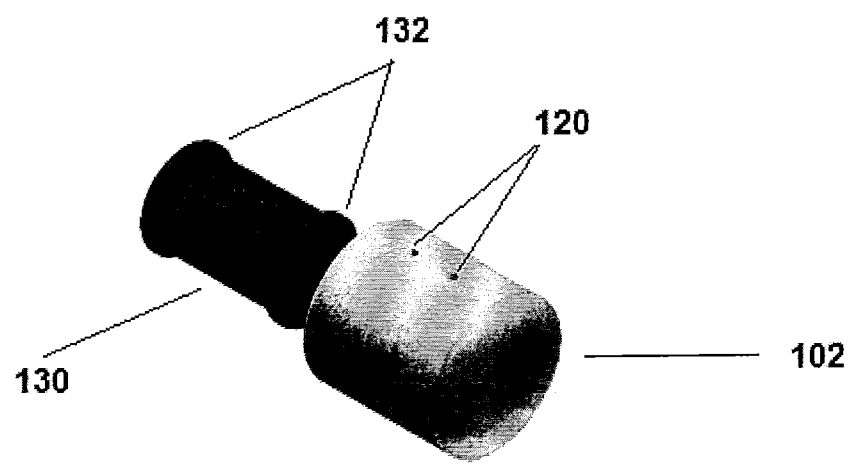
FIG. 6B shows an embodiment of the test cell involving a single pressure transducer with both ends sealed from the pulse, allowing flow in only the radial direction. The two holes along the curved surface of the apparatus allow access for a pressure sensor and connection with the fluid supply.

The test cell 100 may be varied as is known in the art to allow for the flow both the axial and radial directions or in a single direction, for example the radial direction. FIG. 6B shows an embodiment of a reservoir 102 containing barriers 132 on both ends of the sample 130 allowing flow only in the radial direction. The barriers 132 are configured to occupy the dead space between the top portion (reference 106 in FIG. 5B) and the bottom (reference 104 in FIG. 5B) to provide the required seal to isolate the ends of the sample from the pressure pulse. The two holes 120 along the curved surface of the reservoir 102 allow access for monitoring instruments and connection with the permeant supply. FIG. 6A shows an embodiment a reservoir 102 allowing flow in both the axial and radial directions.

The rapid pressure change in the reservoir space also introduces temperature anomalies due to the Joule-Thomson effect and adiabatic expansion, but they typically remain within 0.1-0.2° C. of the equilibrated system temperature and quickly return to the original temperature. Even in the event of non-trivial influences on the pressure data at early times due to these temperature fluctuations, the period where these effects influence the pressure-decay behavior can be neglected in the parameter-estimation scheme, and the initial pulse condition $p_p^*$ can be inferred. Throughout the duration of a test, system temperatures are maintained by placing the system in an incubator capable of maintaining temperatures within ±0.5° C. or a temperature-controlled bath with a rated stability of ±0.01° C.

Leaks are minimized by maintaining the elevated pulse pressure upstream of Valve A throughout the duration of the test, leaving only a small pressure difference across this connection. System leaks take place predominantly through the remaining fixed seals, such as the fittings for the sensors and gas-supply line. The O-ring seal is opened only when changing samples, and is re-greased and/or replaced each time a new sample is analyzed. The fittings to the pressure and temperature sensors and gas supply line, once installed, are rarely broken. As a result, all of the seals tend to have a high degree of integrity, and pressure losses due to leakage occurring during a standard test period are manageable. When necessary, one can account for leakage from the apparatus in a number of ways. A leakage rate can be calculated as the slope of a linear curve fit to late-time data and re-imposed onto the original pressure trace. One can also account for leaks, in the simulations, by modeling them as constant sink terms or as Darcy-like barriers whose permeability changes with pressure. For ease of calculations, the first of these approaches is employed herein.

Figure 5C:
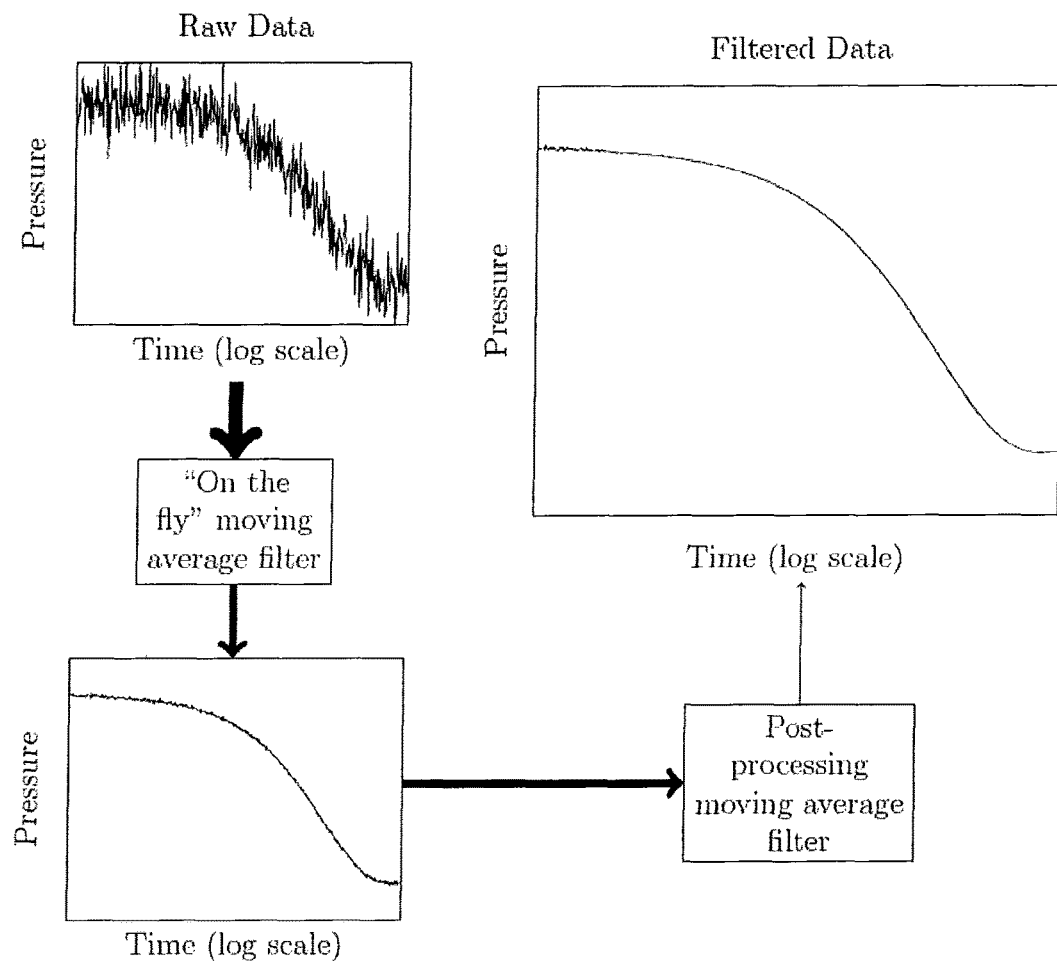
FIG. 5C shows one embodiment of the data-acquisition strategy for full-immersion pressure-pulse decay tests. Line thicknesses are indicative of variance levels of data traces at each stage of the process.

In the present disclosure pressure and temperature data are acquired through a custom platform employing a LabVIEW Real-Time data-acquisition system with a Field Programmable Gate Array (FPGA) interface. One of the main advantages to using this platform is the ability to retrieve, process, and store data at high rates. FIG. 5C gives a schematic of the data acquisition algorithm. For the experiments performed herein data values were typically acquired at a sample rate of 5 kHz, which was the frequency response of the pressure sensor. Acquiring data at such a rate, for a test that may last several hours may seem counterproductive. However, the pressure data are over-sampled at this rate and averaged over a constant window of Y data points (typically 500 values) to produce extremely high-quality output traces. The raw pressure readings $\hat{p}_i$ are fit to a linear trend line, and the intercepts of each line $\hat{p}_j$ are written to a data file. For a given set of Y evenly-spaced pressure readings, the intercept can be calculated with two simple summations and a handful of pre-calculated constants based on the window size Y, as demonstrated by Eq. 7.

$$\hat{p}_j = \frac{2(2Y-1)\sum_{i=1}^{Y} \hat{p}_i - 6\sum_{i=1}^{Y}(i-1)\hat{p}_i}{2Y(2Y-1) - 3Y(Y-1)} \quad (7)$$

Since these are not computationally expensive operations, they can be performed in real-time which enables one to take advantage of rapid acquisition without the need for massive data storage.

Figure 5D:
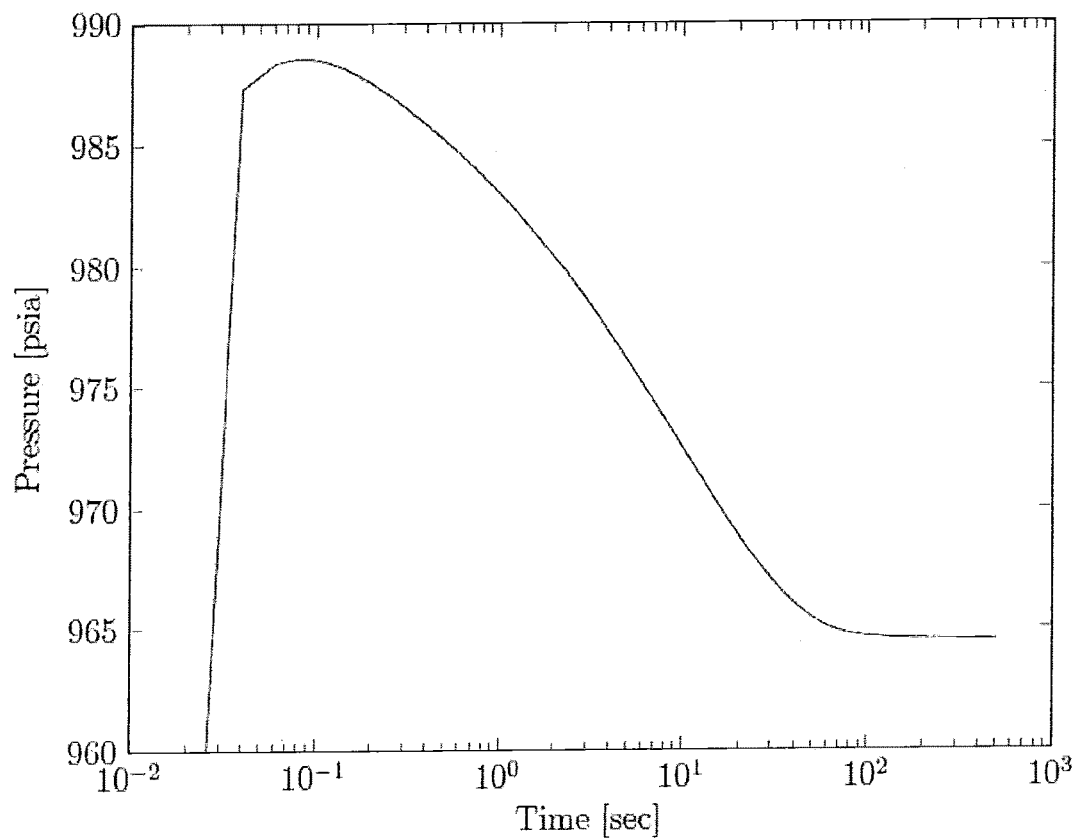
FIG. 5D shows an example pressure trace from a full-immersion pressure-pulse-decay test on a shale sample.

Nonetheless, even at a 10 Hz data-acquisition rate for filtered values (still high enough to resolve early-time phenomena), data sets retrieved from tests spanning several hours, while conveniently small for data storage, would still be prohibitively large to analyze directly. Therefore, during post-processing the data are further reduced using the same averaging algorithm over a set number of logarithmically spaced intervals, yielding traces such as the one shown in FIG. 5D. Arranging the data in such a way provides a good indication of the early-time pressure-decay behavior while giving stronger weight to the higher quality output values at later times. The acquisition algorithm described here meets the high standards on data quality stipulated by the Monte Carlo analyses of the inversion algorithm (FIG. 12).

Since the model is derived for pressures in the "pseudo" domain experimental data must first be converted before performing model inversions. This process begins by fitting the thermophysical properties of interest, namely the viscosity μ, compressibility factor Z and isothermal compressibility c, to a first-order functions of pressure p and temperature T using the equations below. The partial derivatives and planar intercepts in these equations are assumed constant over the limited temperature and pressure range incumbent to most pressure-pulse-decay experiments.

$$\mu \approx \mu_0 + \left(\frac{\partial \mu}{\partial p}\right)_T p + \left(\frac{\partial \mu}{\partial T}\right)_p T \tag{8}$$

$$Z \approx Z_0 + \left(\frac{\partial Z}{\partial p}\right)_T p + \left(\frac{\partial Z}{\partial T}\right)_p T \tag{9}$$

$$c \approx c_0 + \left(\frac{\partial c}{\partial p}\right)_T p + \left(\frac{\partial c}{\partial T}\right)_p T \tag{10}$$

From this point, if desired, one can provide compensation for small changes in temperature that take place by a constant-density analysis, leading to a compensated data trace $\hat{p}_{comp}$ (Eq. 11). Otherwise, one can assume the temperature remains constant throughout the test at a set reference value $T_{ref}$.

$$\hat{p}_{comp} \approx \frac{\left(\frac{\partial Z}{\partial T}\right)_p T_{ref} + Z_0}{\frac{\hat{T}}{T_{ref}} \frac{Z}{\hat{p}} - \left(\frac{\partial Z}{\partial p}\right)_T} \tag{11}$$

Lastly, using a reference temperature either in compensated pressure values or direct pressure measurements, an estimate for pseudo-pressures, which assumes μ and Z are linear functions of p over the limited range of a given test, the pseudo pressure is estimated using Eq. 12.

$$\hat{p}^* = \int_{\hat{p}_0}^{\hat{p}} \frac{p'}{\mu Z} dp' \tag{12}$$

$$\approx \int_{\hat{p}_0}^{\hat{p}} \frac{p' dp'}{\left[\mu_0 + \left(\frac{\partial \mu}{\partial p}\right)_T p' + \left(\frac{\partial \mu}{\partial T}\right)_p T_{ref}\right]\left[Z + \left(\frac{\partial Z}{\partial p}\right)_T p' + \left(\frac{\partial Z}{\partial T}\right)_p T_{ref}\right]}$$

$$= \frac{\log\frac{\mu_0 + \left(\frac{\partial \mu}{\partial p}\right)_T \hat{p} + \left(\frac{\partial \mu}{\partial T}\right)_p T_{ref}}{\mu_0 + \left(\frac{\partial \mu}{\partial p}\right)_T \hat{p}_0 + \left(\frac{\partial \mu}{\partial T}\right)_p T_{ref}}}{\left(\frac{\partial \mu}{\partial p}\right)_T \left[\left(\frac{\partial Z}{\partial p}\right)_T - \frac{Z_0 + \left(\frac{\partial Z}{\partial T}\right)_p T_{ref}}{\mu_0 + \left(\frac{\partial \mu}{\partial T}\right)_p T_{ref}}\left(\frac{\partial \mu}{\partial p}\right)_T\right]} + \frac{\log\frac{z_0 + \left(\frac{\partial Z}{\partial p}\right)_T \hat{p} + \left(\frac{\partial Z}{\partial T}\right)_p T_{ref}}{z_0 + \left(\frac{\partial Z}{\partial p}\right)_T \hat{p}_0 + \left(\frac{\partial Z}{\partial T}\right)_p T_{ref}}}{\left(\frac{\partial Z}{\partial p}\right)_T \left[\left(\frac{\partial \mu}{\partial p}\right)_T - \frac{\mu_0 + \left(\frac{\partial \mu}{\partial T}\right)_p T_{ref}}{Z_0 + \left(\frac{\partial Z}{\partial T}\right)_p T_{ref}}\left(\frac{\partial Z}{\partial p}\right)_T\right]}$$

The following is an application of the full immersion pressure-pulse decay on a cylindrical core sample. A cylindrical sample of length L, diameter D and porosity n is placed in a reservoir of volume $V_r$ such that its entire outer surface area is exposed to the permeant in the reservoir using the apparatus of FIGS. 5A and 5B. The internal pore pressure p of the sample as well as the pressure in the surrounding reservoir $p_r$ are equilibrated to a level of $p_0$. The reservoir pressure was instantaneously pulsed to a slightly higher (typically 5-10%) level of $p_p$. Assuming the permeabilities in the axial (x) and radial (r) directions to be the primary axes of permeability, with principal values of $k_x$ and $k_r$, respectively, the pressure-decay behavior after the instantaneous pulse can be modeled in a sufficiently simple manner by a combination of the differential form of Darcy's Law and the continuity equation using Eq 1 to 6 discussed above.

Experimental data were obtained. Pressure and temperature data are recorded through a National Instruments CompactRio system employing the FPGA interface, allowing for custom control of high throughput data collection. Data are recorded and analyzed for a pressure-pulse-decay tests, where recording early-time behavior is important, but tests last an indeterminable amount of time.

The equations are solved numerically using an explicit finite-difference scheme with fourth-order temporal accuracy and second-order spatial accuracy. In this form, the primary influential parameters of interest are $\tau_R$ (defined in Eq. 2), $\lambda_x^2$ (Eq. 3) and $\gamma_r$. Once the set of these parameters that best fit the results of these solutions to experimental data are determined, the parameters of interest (i.e. n, $k_r$ and $k_x$) can readily be calculated using Eq. 1 to 6 above and $$\gamma \equiv \frac{V}{n\pi R^2 L}$$

Example 2—Determination of Initial Estimates for Porosity and Radial Permeability If flow is limited to only the radial direction by sealing the circular end faces of the sample from the permeant, the pressure response to a pulse-decay experiment can be modeled using the boundary-value problem defined in Equations (13)-(16).

$$\frac{\partial p_D^*}{\partial t_{D,R}^*} = \frac{1}{r_D}\frac{\partial p_D^*}{\partial r_D} + \frac{\partial^2 p_D^*}{\partial r_D^2} \quad (13)$$

$$p_D^*(r_D, x_D, t_{D,R} = t_{D,R}^* = 0) = \begin{cases} 0, & 0 \le r_D < 1 \\ 1, & r_D = 1 \end{cases} \quad (14)$$

$$\left.\frac{\partial p_D^*}{\partial r_D}\right|_{r_D=0} = 0 \quad (15)$$

$$\left.\gamma\frac{\partial p_D^*}{\partial t_{D,R}^*}\right|_{r_D=1} = -\left.\frac{\partial p_D^*}{\partial r_D}\right|_{r_D=1} \quad (16)$$

Such a flow scenario sufficiently simplifies the governing equations to resolve their solution analytically. The solution for the internal pressure response $p_D^*$ and the response in the reservoir $p_D^*|_{r_D=1}$ are given below as Equations (17) and (18), respectively. Note that these solutions are infinite sums that are very closely approximated by truncation to a reasonable number of terms, each of which are dependent upon $\phi_m$, defined as the $m^{th}$ positive root to Equation (19).

$$p_D^* = \frac{\gamma}{1+\gamma} + \sum_{m=1}^{\infty} \frac{e^{-\phi_m^2 t_{D,R}} J_0(\phi_m r_D)}{J_0(\phi_m)\left(\frac{1+\gamma}{\gamma} + \frac{\gamma\phi_m^2}{4}\right)} \quad (17)$$

$$p_D^*|_{r_D=1} = \frac{\gamma}{1+\gamma} + \sum_{m=1}^{\infty} \frac{e^{-\phi_m^2 t_{D,R}}}{\frac{1+\gamma}{\gamma} + \frac{\gamma\phi_m^2}{4}} \quad (18)$$

$$\frac{J_1(\phi_m)}{J_2(\phi_m)} + \frac{\gamma\phi_m}{2} = 0 \quad (19)$$

Using a finite-difference scheme detailed above, the reservoir pressure profile from a full-immersion pressure-pulse-decay (whose governing equations are outlined in Eqs. 1-6) is plotted for multiple values of $\lambda_x^2$ and $\gamma$ in FIG. 4. The cases of $\lambda_x^2=0$ (shown in solid black lines) are produced using the analytical solution to the radial flow problem, Eq. (18), which demonstrates good agreement between the two models. What is most noteworthy here is that, in all cases, the pressure decays to its equilibrium value within one time constant, $\tau_R$. As reference, for a cylindrical sample one-inch in diameter and one-inch length, this time constant equals roughly 6 hours for a 1 nanodarcy radial permeability using a gaseous permeant such as $N_2$ or He at 1000 psia initial pressure. For the shales having 100 nanodarcy permeabilities, which are of most interest to the oil and gas industry, $\tau_R \approx 5$ minutes.

Figure 7:
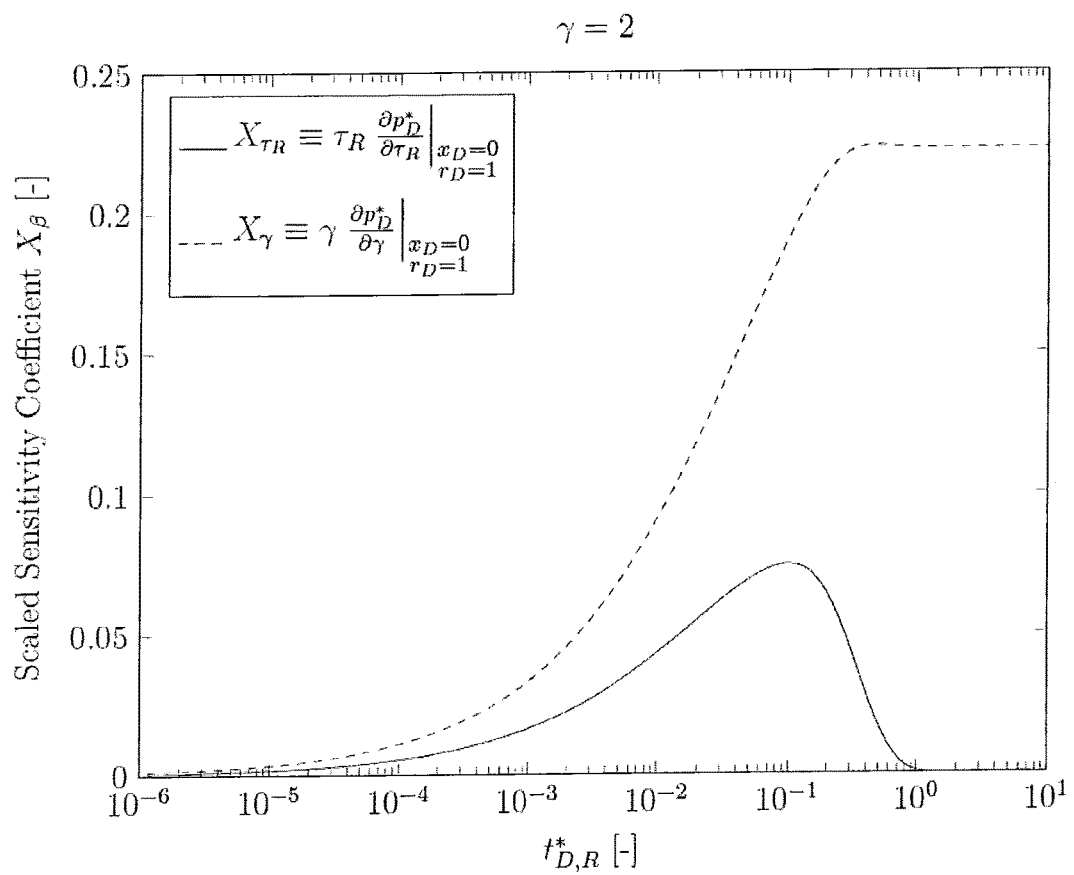
FIG. 7 shows a comparison between the scaled sensitivity coefficients of the radial-flow model to $\gamma_r$ and $\tau_R$.

One of the most significant challenges for this methodology is the determination of a unique set of parameters that best fit the model output to experimental data. In order to do so, the scaled sensitivity coefficients for each parameter should not have great disparities in magnitude compared to one another. To address this point, FIG. 7 shows that, under purely radial conditions, the sensitivity of the model output to $\gamma$ greatly exceeds the model sensitivity to $\tau_R$. Therefore, $\gamma$ can be independently estimated based on the final equilibrium value, which equals $$\frac{\gamma}{1+\gamma}.$$

Figure 8:
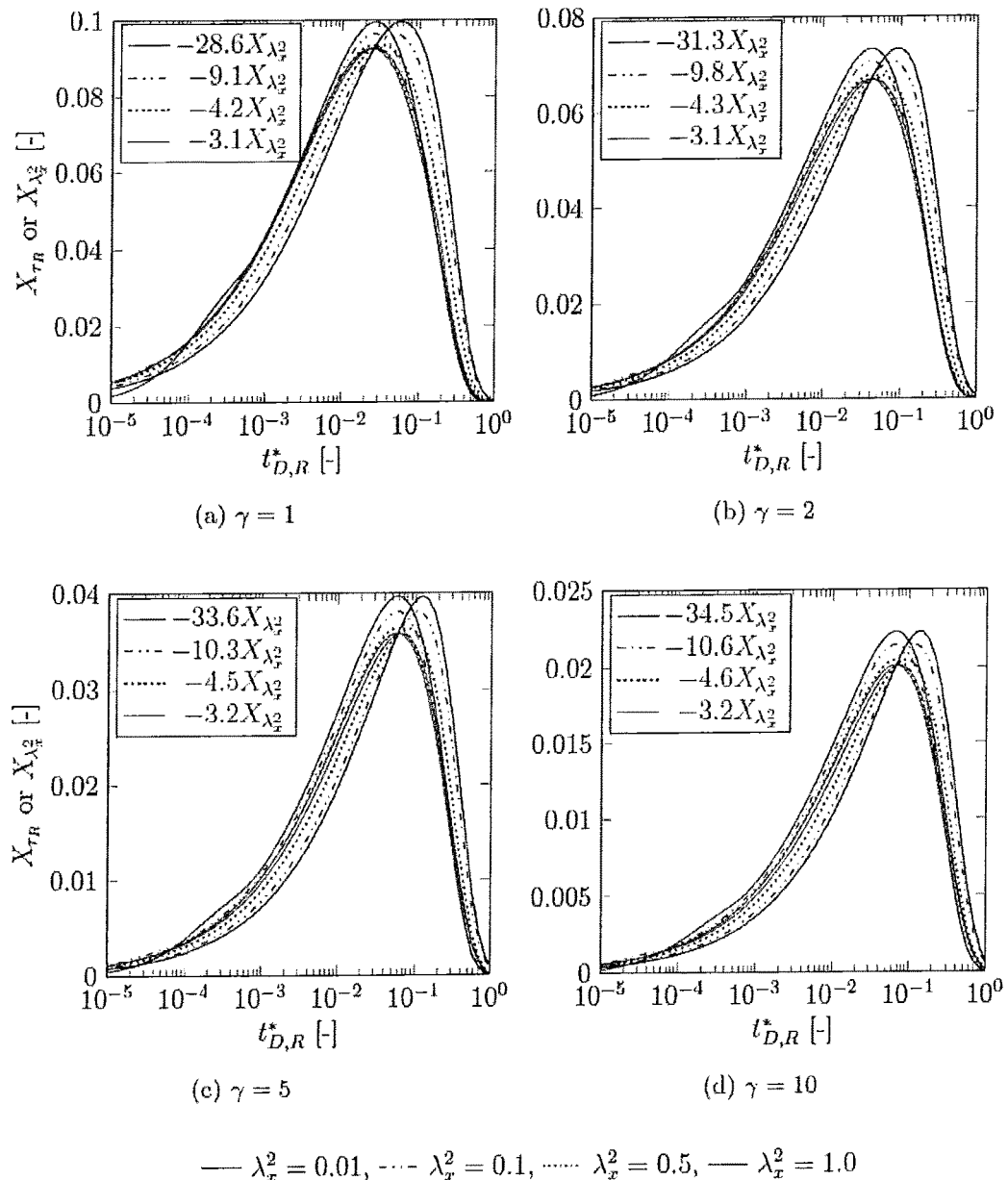
FIG. 8 shows Comparison between scaled sensitivity coefficients with respect $\tau_R$ and $\lambda_x^2$. The case of strong parameter correlation ($\lambda_x^2=1$) displays both sensitivities (X$\tau_R$ and X$\lambda_x^2$) in red. Intermediate cases ($0.1 \le \lambda_x^2 \le 0.5$) are presented to display the trend toward correlation.

The remaining parameters can then be estimated using standard non-linear assessment algorithms (e.g. nonlinear Least Squares, Steepest Decent Methods, Levenberg-Marquardt). Another important consideration for uniqueness is that scaled sensitivity coefficients should be linearly independent of one another. FIG. 8 show a comparison between these coefficients for $\tau_R$ and $\lambda_x^2$. While the disparity in magnitude between the sensitivities to $\tau_R$ and $\lambda_x^2$ increases at smaller values of $\lambda_x^2$, their curves suggest linear independence. On the other hand FIG. 8 shows that, while the disparities in magnitude decrease as $\lambda_x^2$ increases, the two sensitivity coefficients become much more aligned (i.e. linearly dependent).

As one would expect $\lambda_x^2 \ll 1$ for most materials of interest, particularly layered media such as shales, the parameter-estimation procedure begins by assuming $\lambda_x^2=0$ and modeling experimental data with Eq. (18) to estimate $\gamma$ and provide an educated initial guess for $\tau_R$. Using this initial guess, $\tau_R$ and $\lambda_x^2$ are estimated using the numerical solution to Equations (1)-(6).

Example 3—Inversion Strategy

In order to leverage the advantages of the proposed experimental scheme, one must establish a straightforward protocol for interpreting its data. At the outset, there arises the seemingly non-trivial task of determining a unique set of parameters that yield the best fit to a given set of experimental data. The sensitivity of each parameter of interest to the model output is investigated in this Example. That investigation then leads to a robust algorithm and design of experiment with which to provide accurate estimates of sample properties over a wide range of anticipated outcomes.

Figure 9:
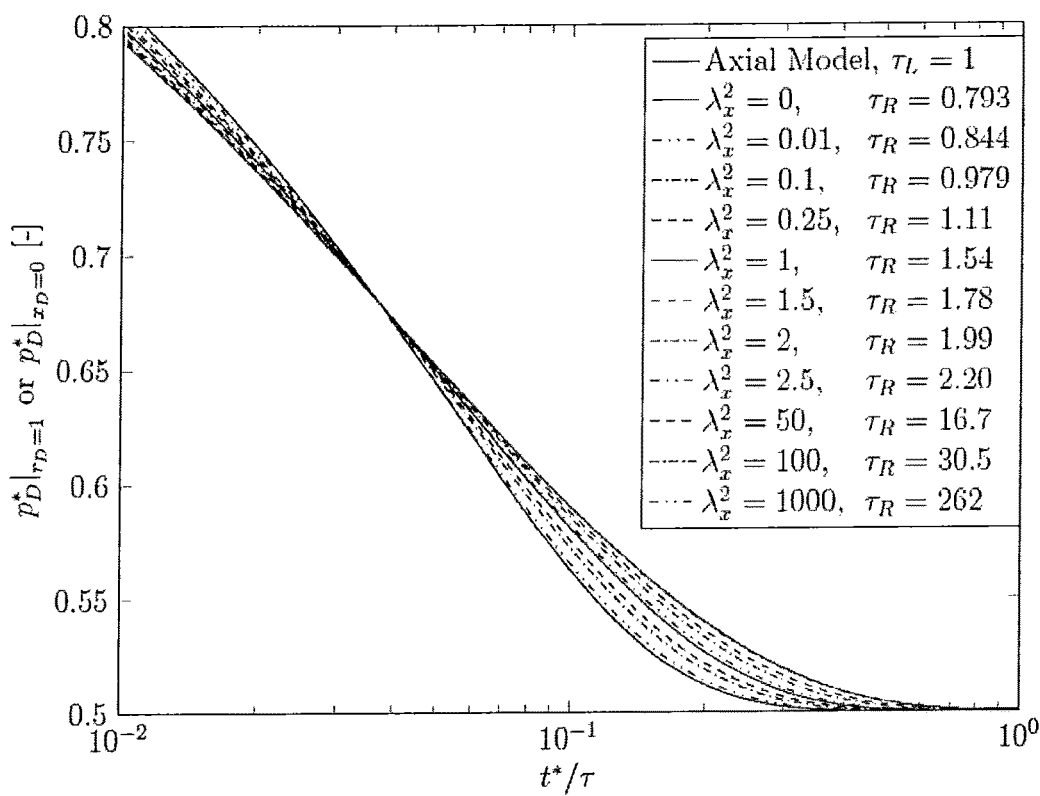
FIG. 9 shows curve fits to axial-ow case (shown in solid black). Note that the purely radial ow case (shown in solid blue) was generated using the analytical solution provided in Eq. 12.

The pressure response from the homogeneous bi-directional pulse-decay with equally sized reservoir volumes ($\gamma_0=\gamma_1=0.5$, $\tau_L=1$) is displayed (shown in solid black) as a pure axial-ow case of the full-immersion pressure-pulse decay (FIG. 9). Full-immersion models with equivalent reservoir volumes ($\gamma=1$) and increasing degrees of axial-flow influence (or increasing values of $\lambda_x^2$) are fit to the axial model by changing the time constant $\tau_R$ ($t^*_{D,R} \equiv t^*/\tau_R$, $\tau_R$ defined in Eq. 2).

Due to differing flow-domain geometries, the case of pure radial flow (Eq. 18, shown in solid blue) is incapable of fitting the axial-flow case without characteristic differences between their pressure profiles. Incremental changes to $\lambda_x^2$ from the radial case (i.e., the remaining curves shown in blue) yield small but distinguishable deviations from the axial case. At intermediate values of $\lambda_x^2$ (curves shown in red), the curve fits are no longer distinguishable as they have reached the maximum deviation from the pure axial-flow case. With cases of stronger axial-flow influence (shown in black) the model outputs approach the axial flow case until, at sufficiently large values of $\lambda_x^2$ they match the axial-flow case exactly, again giving credence to the models. These preliminary analyses indicate that under realistic permeability ratios ($0 \le \lambda_x^2 \le 1$), the full-immersion model could provide a unique fit to a given data set.

Example 4—Sensitivity Study

The primary indicator of the uniqueness of a parameter-set estimate, when fitting a model to experimental data, is the level of linear independence exhibited by the sensitivity to each parameter. Linear dependence among a given set of parameter sensitivities implies correlation of those parameters. Making such assessments involves comparison of the scaled sensitivity coefficients of each parameter. A wide range of conventions exists throughout the literature for defining these. The convention chosen here to define the scaled sensitivity coefficient for a given model output f with respect to the parameter $\beta$ is given in Eq. 20.

$$X_\beta \equiv \beta \frac{\partial f}{\partial \beta} = \frac{\partial f}{\partial \log \beta} \quad (20)$$

Since the units of the scaled sensitivity coefficient for all parameters of interest match those of the dependent variable, they provide a direct comparison to one another when gauging the degree of linear independence. They also provide a clear comparison to the range of the dependent variable, to gauge their level of sensitivity to the model output. The following paragraphs provide comparisons of scaled sensitivity coefficients of the predicted decay in reservoir pressure with respect to the following normalized parameters of interest for the full-immersion model.

1. The radial-flow time constant $\tau_R$, defined by Eq. 2.
2. The reservoir-to-pore volume ratio, $\gamma$
3. The axial-to-radial permeability ratio $\lambda_x^2$, defined in Eq. 3.
4. The initial pulse pressure in the pseudo-pressure domain $p_p^*$, defined by Eq. 21 ($p \rightarrow p_p$).

$$\hat{p}^* \equiv \int_{p_0}^{p} \frac{p'}{\mu Z} dp' \quad (21)$$

The choice of the last parameter listed above, to be discussed further below, is as a "nuisance parameter" to account for early-time phenomena which are not taken into account by the flow model. Having accurate estimates of these parameters, one can readily calculate the porosity n and directional permeabilities $k_r$ and $k_x$ of the sample.

Figure 10:
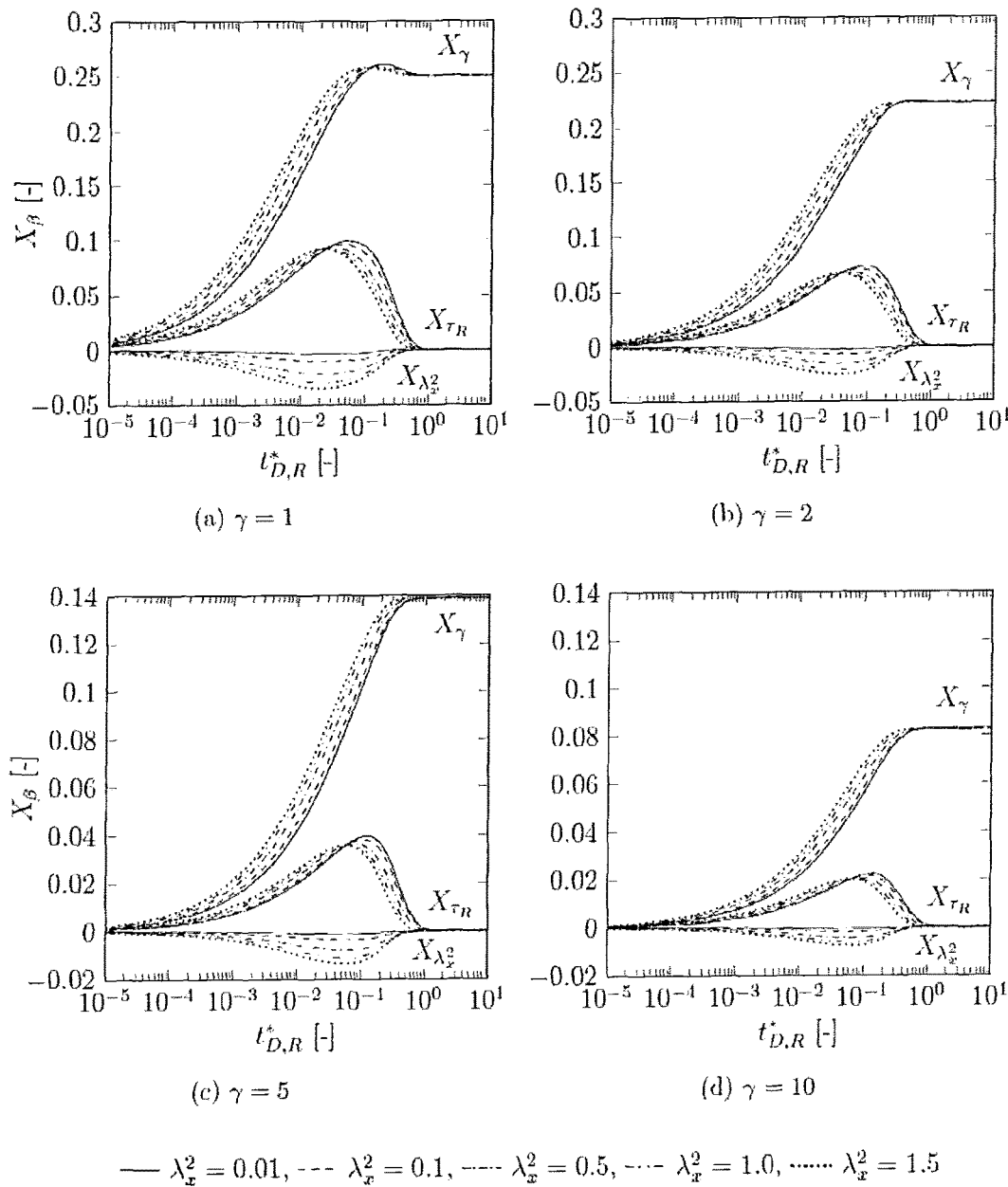
FIG. 10 shows scaled sensitivity coefficients of the full-immersion pressure-pulse decay over a wide range of anticipated parameters.

FIG. 10 provides plots of the scaled sensitivity coefficients ($X\tau_R$, $X\gamma$ and $X_{\lambda_x^2}$) with respect to the three parameters listed above for a wide range of anticipated outcomes ($1 \le \gamma \le 10$ and $0.01 \le \lambda_x^2 \le 1.5$). These indicate that the influence of $\gamma$, which in all cases is greater than those of the remaining parameters, imposes a unique signature on the pressure behavior. Meanwhile, the effect of $\lambda_x^2$, which is the least influential of all parameters, increases in magnitude as its value increases. $\lambda_x^2$ appears to have a similar shape (albeit opposite in sign) as the sensitivity to $\tau_R$, which would indicate linear dependence between the two. Note that while choosing relevant values of $\gamma$ and $\lambda_x^2$ is important for this analysis, the choice of $\tau_R$ and $P_p^*$ is immaterial, as their sensitivity coefficients are only functions of the remaining parameters listed above (see Eq. 22 and 23).

$$X_{\tau_R} \equiv \tau_R \frac{\partial p_D^*}{\partial \tau_R} = \tau_R \frac{\partial t_{D,R}^*}{\partial \tau_R} \frac{\partial p_D^*}{\partial t_{D,R}^*} = -t_{D,R}^* \frac{\partial p_D^*}{\partial t_{D,R}^*} = -t^* \frac{\partial p_D^*}{\partial t^*} \quad (22)$$

$$X_{p_p^*} \equiv p_p^* \frac{\partial p_D^*}{\partial p_p^*} = -p_D^* \quad (23)$$

The independence of these sensitivity coefficients from their respective parameters has the added advantage of significantly decreasing the computational resources required to make parameter estimates. The most rigorous portion of most estimator schemes, including the ones employed for this study, is the calculation of the Jacobian matrix X, whose columns represent the sensitivity coefficients with respect to each parameter. Calculating these values typically requires and numerical partial derivative estimate by way of a separate instance of the forward model (described in more detail herein). However, since the numerical discretization scheme calculates the temporal partial derivative $$\frac{\partial p_D^*}{\partial \tau_R}$$

at each time step (described in more detail herein), each run of the forward model can also output $X_{\tau_R}$, and $X_{p_p^*}$.

Figure 11:
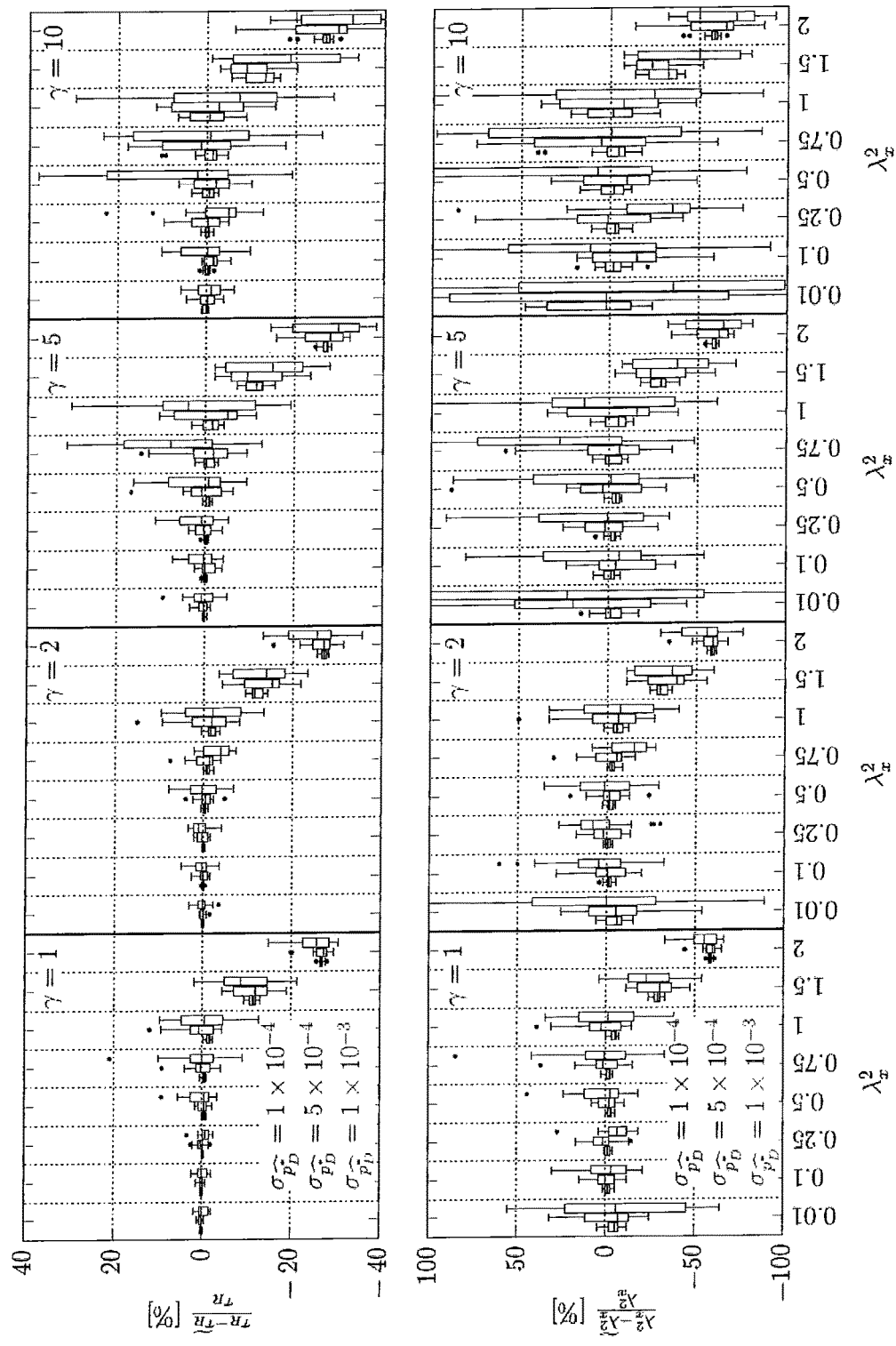
FIG. 11 shows results of Monte Carlo simulations for the flow model of the full immersion pressure-pulse decay, which demonstrates the conditions required for accurate parameter estimates $\sigma_{\tilde{P}^*_p} \leq 1\times 10^{-3}$, $0.01 < \lambda_x^2 < 1$, $\gamma \leq 10$).
Figure 12A:
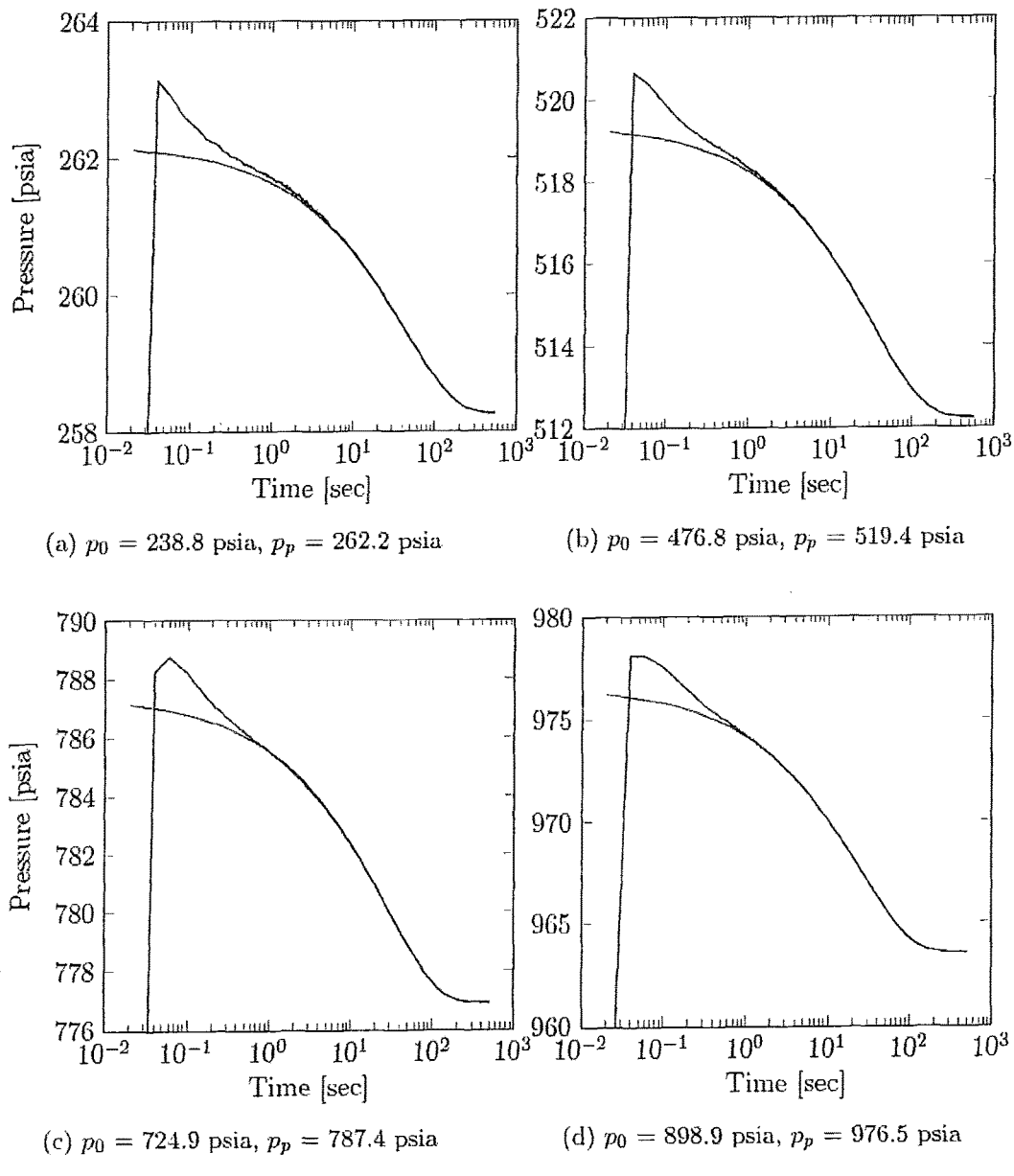
FIG. 12A shows a history match between experimental data and model for sample UAB-1.
Figure 12B:
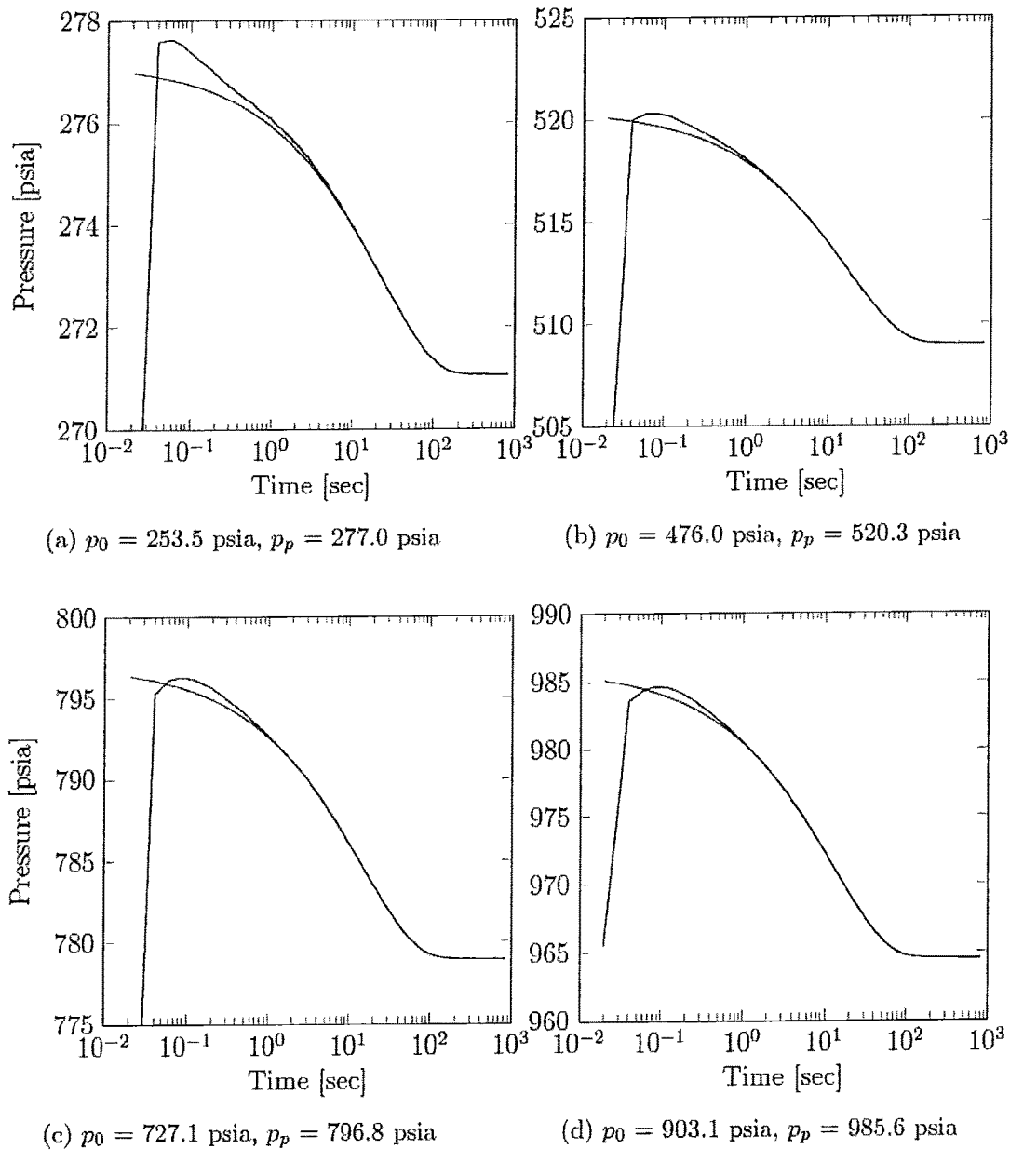
FIG. 12B shows a history match between experimental data and model for sample UAB-1.
Figure 12C:
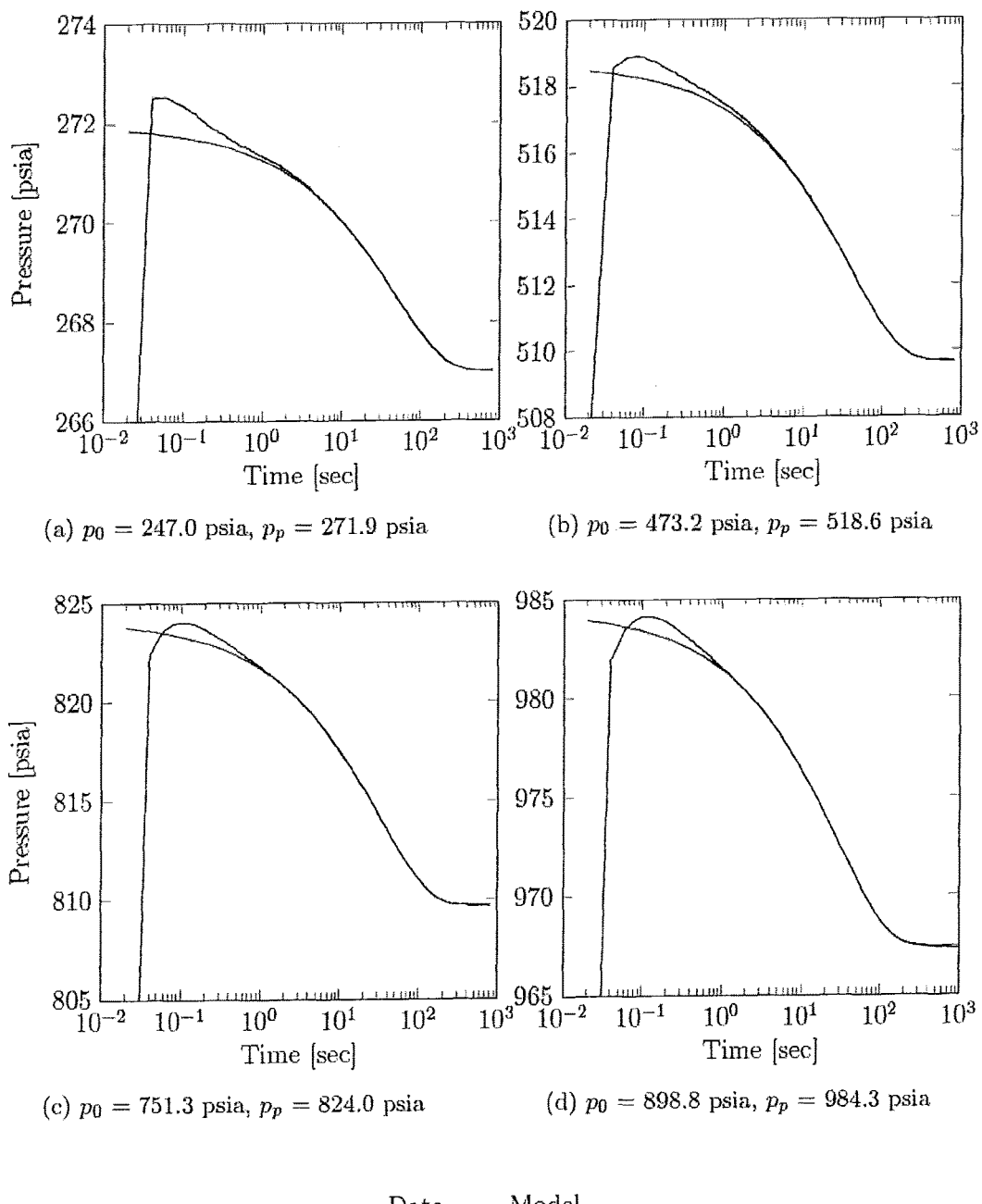
FIG. 12C shows a history match between experimental data and model for sample UAB-1.
Figure 12D:
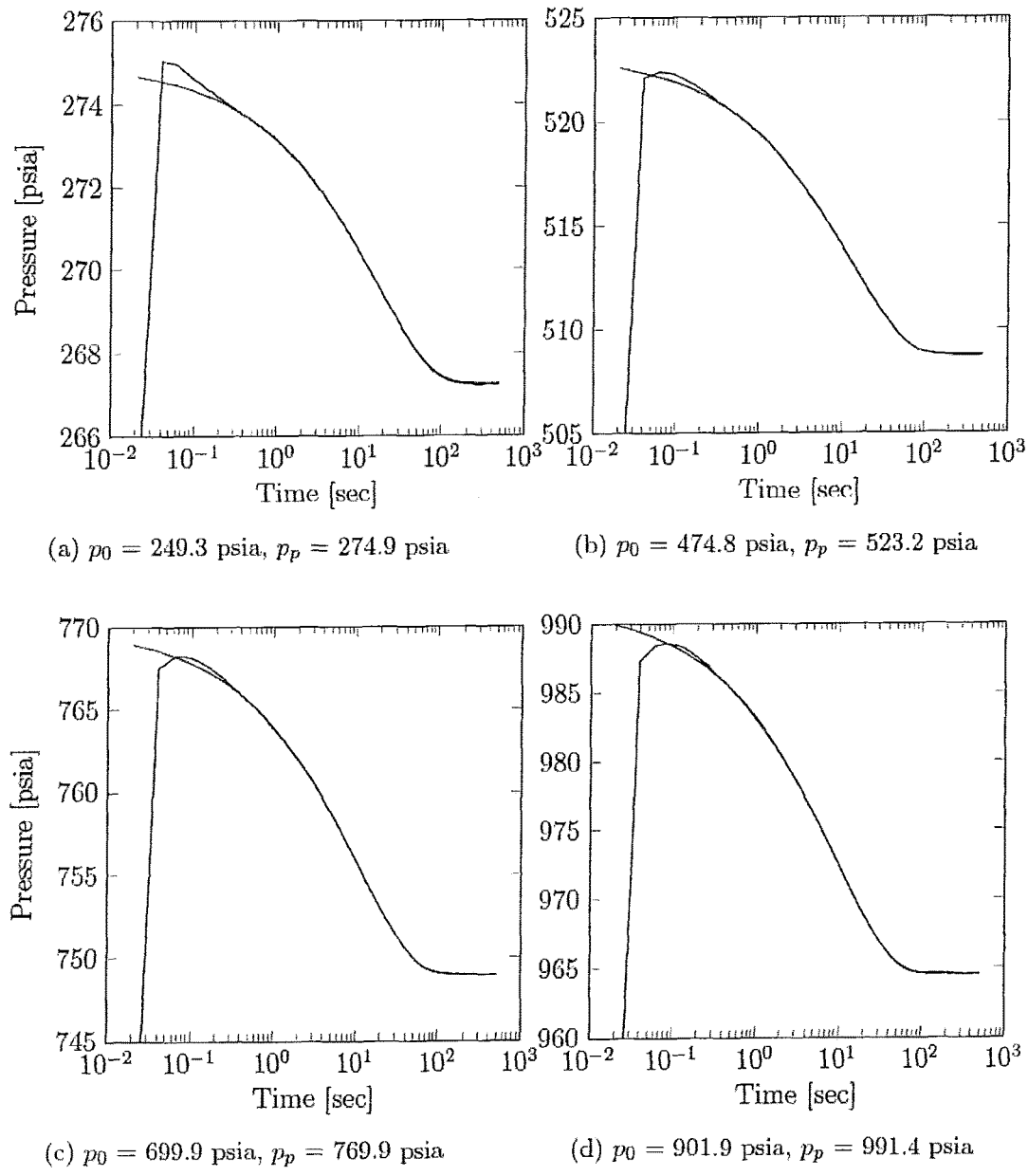
FIG. 12D shows a history match between experimental data and model for sample UAB-1.

Correlations between $\tau_R$ and $\lambda_x^2$ are investigated more closely in FIG. 11. These plots compare the model sensitivity to $\tau_R$, $X\tau_R$, with an amplified, opposite version of its sensitivity to $\lambda_x^2$, $X_{\lambda_x^2}$ (multiplier listed in the legend of each plot) to study their implications on parameter correlation. From these, it is noted that the sensitivity plots bear stronger resemblance to one another with increasing $\lambda_x^2$, until they become almost indistinguishable in the case of $\lambda_x^2=1$ (curves shown in red). While they are most easily distinguished at smaller values of $\lambda_x^2$, the relatively small magnitude of $X_{\lambda_x^2}$ under these conditions (quantified by the increasing magnitude of the multiplier in the legends) also limits the ability of the inversion scheme to calculate this parameter accurately. Thus, as discussed herein, a parameter estimator for this flow model is best suited for cases of $0.01 < \lambda_x^2 < 1$. However, a parameter estimator in the range $0.01 < \lambda_x^2 < 1$ is not required for operation of the methods described herein.

Example 5—Characterization of Method Boundaries

To provide a comprehensive understanding of the ability to provide solutions that are unique and accurate, Monte Carlo analyses were performed on the model inversion algorithm outlined in FIG. 3. In total, 32 forward models were run at very high spatial resolution (300×300 grid points) to simulate pressure data over a wide range of parameters ($0.01 \le \lambda_x^2 \le 2$, $1 \le \gamma \le 10$). For each of these flow conditions, a normal distribution of random errors with increasing standard deviation ($\sigma_{p_D^*}$) was imposed on the model output to generate synthetic data under these conditions. For each flow condition at each standard deviation, 20 curve fits were acquired from 20 different error distributions.

Comparisons between the estimated parameters $\tau_R$ and $\lambda_x^2$ (indicated by ~) and their corresponding true values are provided by the box and whiskers plots in FIG. 11. Highly accurate estimates were acquired for the remaining parameters ($\gamma$ and $p_p^*$ for all cases, so their analyses are not provided here. At the smallest standard deviation ($1 \times 10^{-4}$ shown in black), estimates in cases of $0.01 \le \lambda_x^2 \le 1$ are reasonable, with deteriorating quality with increasing $\gamma$ and decreasing $\lambda_x^2$. Yet even at this low error level, the inversion appears to provide negatively biased estimates of $\tau_R$ and $\lambda_x^2$ (indicated by ~) when $\lambda_x^2$ surpasses unity. This is due to the parameter-correlation issues. The decreasing estimate accuracy with increasing $\gamma$ and decreasing $\lambda_x^2$ which is highlighted more in estimates of $\lambda_x^2$ than in estimates of $\tau_R$ amplifies with errors of increasing standard deviation (from $1 \times 10^{-4}$ to $5 \times 10^{-4}$ to $1 \times 10^{-3}$).

Example 6—Analysis of Whole Core Cylindrical Samples

A new experimental methodology on whole-core cylindrical samples has been developed that simultaneously determines the porosity and apparent permeabilities parallel and perpendicular to the native bedding planes from a single test on a single cylindrical core sample. Using the full immersion pressure-pulse decay, radial and axial permeabilities from a set of standard plug samples were determined in the sub-microdarcy regime within 5-10 minutes. Another set of samples, having permeabilities in the sub-nanodarcy range, were analyzed by tests lasting approximately 6-24 hours.

Core samples for analysis were obtained from various sources, including shale materials from the Ft. Worth Basin in West Texas in collaboration with Oklahoma State University and from an outcrop formation courtesy of Weatherford Laboratories. Samples from the latter source were measured independently by Weatherford to compare against currently available permeametry techniques. The nature of the experimental data, specifically the imperfections causing deviation from the model and the measures taken to mitigate them, are described. Next, results from multiple samples are presented, including comparison plots between experimental data and model output. Four cylindrical sample were plugged from an outcrop formation by Weatherford Laboratories. After drying them, independent measurements were performed by Weatherford personnel to ascertain porosity and permeability.

For each sample acquired from Weatherford, a series of four experiments were performed with Helium gas at different pressure levels, ranging from approximately 250 to 1000 psia. Data from all four tests were fit simultaneously to the flow model, which treated the apparent permeabilities parallel to bedding ($k_r$; radial permeability) and perpendicular to bedding ($k_x$; axial permeability) as constants for each test. These values varied from test to test via Eqs. 24 and 25 to account for gas-slippage (or "Klinkenberg") effects. Note that the reference pressure pref for each test was chosen as its average value recorded over the duration of the test. The porosity n is assumed constant for all tests performed on the same sample.

$$k_r = k_{\infty,r}\left(1 + \frac{b_r}{p_{ref}}\right) \quad (24)$$

$$k_x = k_{\infty,x}\left(1 + \frac{b_x}{p_{ref}}\right) \quad (25)$$

The resulting parameter estimates for each of the four core samples (labeled UAB-1 to UAB-4) are given in Table 1. These estimates yield history matches (a comparison between experimental data and model outputs for tests performed on a sample). FIGS. 12A-D shows a history match for samples UAB-1 to UAB-4, respectively. Parameter uncertainties are also provided in Table 1, which indicate the accuracies of $k_{\infty,x}$ and $b_x$ estimates are much lower than those of $k_{\infty,r}$ and $b_r$. The highest uncertainties can be alleviated by performing tests at higher pressure, by decreasing the diameter of the sample to equal its length and, if necessary, by performing a unidirectional test, such as using conventional pressure-pulse decay or any other method known in the art.

TABLE 1

| Core | D [in] | L [in] | Result | | | |
|---|---|---|---|---|---|---|
| UAB-1 | 1.490 | 0.940 | n: | 4.85 | +0.05% / −0.05% | % |
| | | | $k_{\infty,r}$: | 88.7 | +9.06% / −8.31% | nd |
| | | | $b_r$: | 476 | +26.4% / −20.9% | psia |
| | | | $k_{\infty,x}$: | 14.3 | +86.0% / −46.3% | nd |
| | | | $b_x$: | 4020 | +154% / −60.7% | psia |
| UAB-2 | 1.498 | 0.980 | n: | 6.75 | +0.06% / −0.06% | % |
| | | | $k_{\infty,r}$: | 225 | +5.76% / −5.44% | nd |
| | | | $b_r$: | 397 | +19.2% / −16.1% | psia |
| | | | $k_{\infty,x}$: | 23.1 | +74.8% / −42.8% | nd |
| | | | $b_x$: | 3864 | +97.2% / −49.3% | psia |
| UAB-3 | 1.476 | 0.993 | n: | 4.70 | +0.05% / −0.05% | % |
| | | | $k_{\infty,r}$: | 67.6 | +8.96% / −8.22% | nd |
| | | | $b_r$: | 540 | +23.5% / −19.0% | psia |
| | | | $k_{\infty,x}$: | 5.39 | +214% / −68.1% | nd |
| | | | $b_x$: | 6160 | +264% / −72.5% | psia |
| UAB-4 | 1.490 | 0.999 | n: | 7.59 | +0.04% / −0.04% | % |
| | | | $k_{\infty,r}$: | 306 | +11.1% / −9.96% | nd |
| | | | $b_r$: | 424 | +30.8% / −23.6% | psia |
| | | | $k_{\infty,x}$: | 57.2 | +80.8% / −44.7% | nd |
| | | | $b_x$: | 2260 | +116% / −53.6% | psia |

Figure 13:
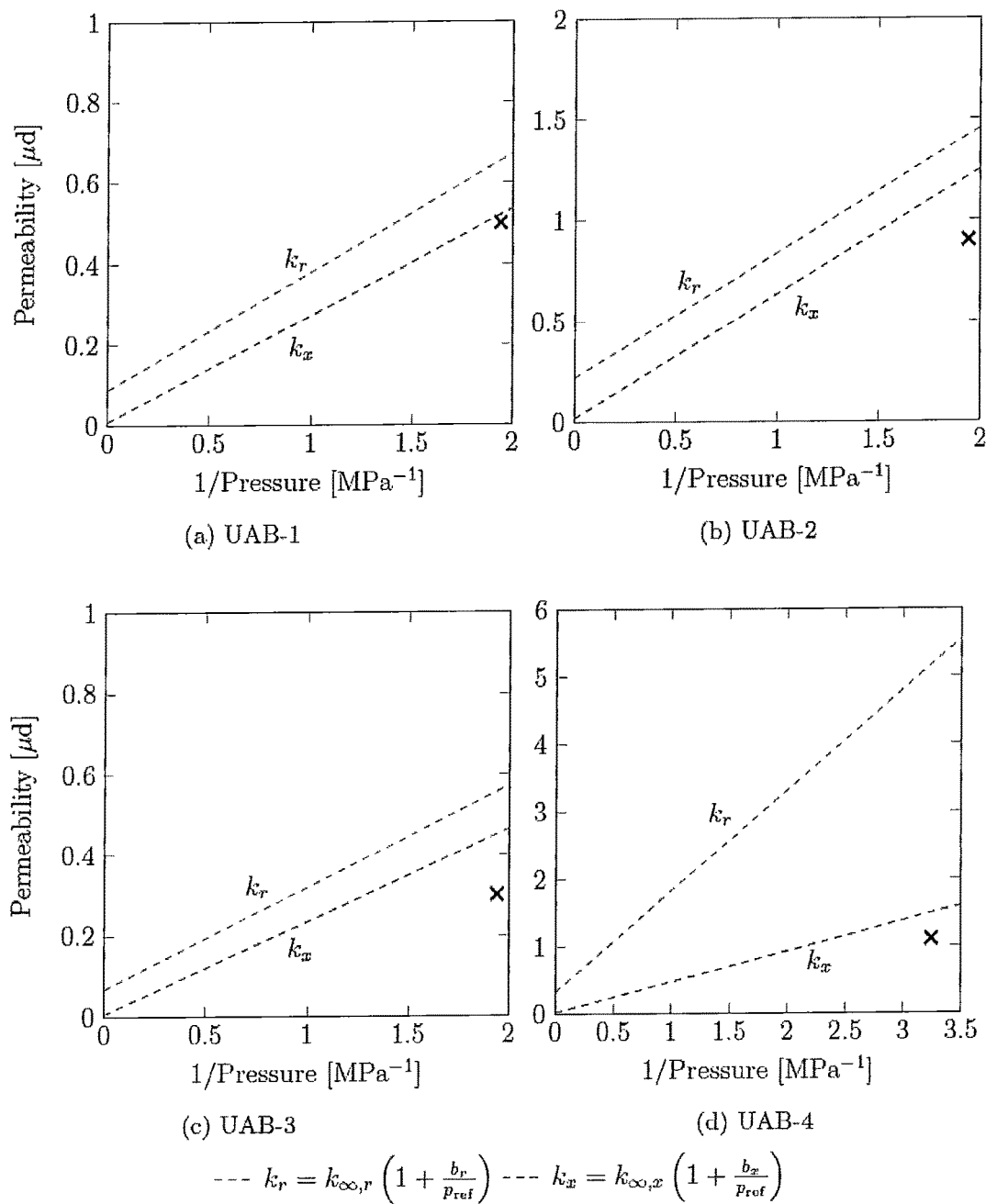
FIG. 13 shows Klinkenberg plots for apparent permeabilities parallel ($k_r$) and perpendicular ($k_x$) to bedding of the four cylindrical samples (UAB-1 to UAB-4).

Klinkenberg plots relating apparent permeabilities ($k_r$ and $k_x$) to inverse pressure for each sample UAB-1 to UAB-4 are given in FIG. 13. These plots show good agreement with the independent assessments of $k_x$ performed by Weatherford at a test pressure of 60 psig (shown by X). For each case, the estimate provided by Weatherford falls below the predicted value using the full immersion approach. However, this discrepancy can be explained (at least in part) experimentally due to the difference in confining stresses between the two experiments. Weatherford estimates were acquired by confining the sample with a net stress of 500 psi, while full-immersion tests were performed with the samples unconfined.

In this case, the upper bounds of permeabilities perpendicular to bedding were constrained to be less than those parallel to bedding. Given the excellent agreement between the model output and experimental data (see FIGS. 12A-D), large uncertainties can only arise from parameter correlation. These correlation effects are manageable so long as the factor $\lambda_x^2$ remains less than 1. The experimental apparatus was designed for wider (i.e., D>L) sample geometries in anticipation of apparent permeability ratios $k_x/k_r$ maintaining $\lambda_x^2$ well under this limit at all test pressures. However, it appears the mechanism driving the ratio down is the large Klinkenberg coefficient $b_x$. Thus, lower ratios are only encountered with sufficiently high pore pressure, which were above the 1000 psia rated pressure of the test cell used in the current experiment.

The methods described provide an accurate estimate of $k_r$ and $k_x$, but $k_x$ estimates can only provide accurate upper and lower bounds. A number of intervention strategies may be used to narrow these uncertainty windows, such as, but not limited to:

1. accounting for non-linear trends in apparent permeability (i.e., Knudsen diffusion);
2. decreasing the diameter-to-length ratio (D=L) of the sample;
3. performing tests at higher pressure; and
4. performing an additional unidirectional test (as described herein).

Each of the foregoing may be used in combination with the full immersion pressure-pulse decay methods described herein.

Example 7—Further Experimental Interventions to Improve Robustness

In certain embodiment, the conditions under which a unique set of parameters can be determined require a highly accurate data (standard deviation≤1×10⁻³), a sufficiently small reservoir volume ratio ($\gamma$<10) and a dimensionless permeability ratio $\lambda_x^2$ that is neither too small or too large (for example, $0.01 \leq \lambda_x^2 \leq 1$). Even under these conditions, the uncertainty of the parameters may still exceed those required by interested parties (for example, see Example 5 and FIG. 11). Therefore, in this event or the event that the experimental conditions lie outside of those required to provide accurate estimates described above, experimental interventions should be taken to ensure sufficient accuracy.

Figure 14:
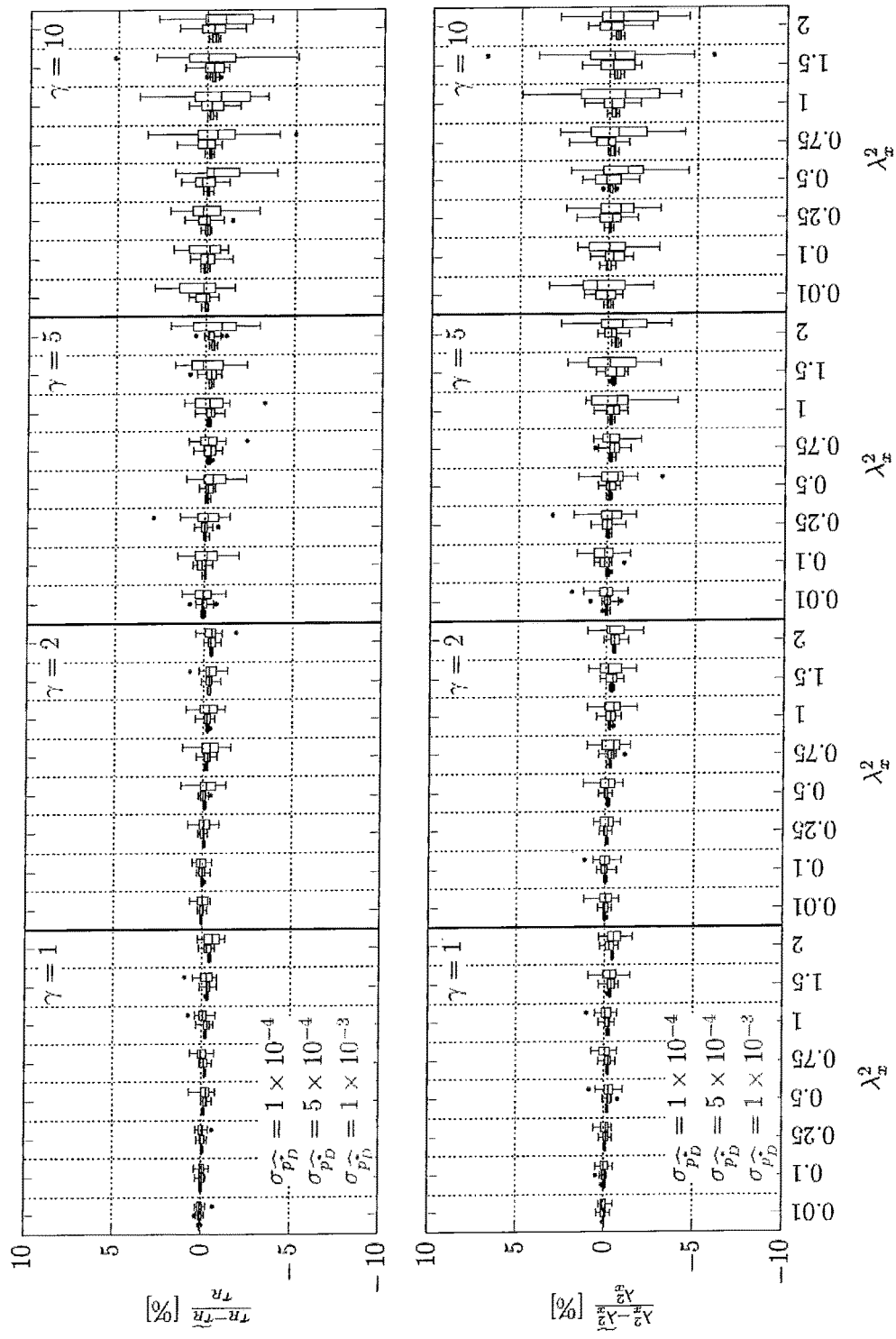
FIG. 14 shows results of Monte Carlo analyses of a full immersion pressure-pulse decay combined with a bi-directional axial pulse-decay experiment. Under all the conditions shown (which match those shown in FIG. 12) all parameters are estimated within 5% of their true values).

One such strategy would be to combine analysis of a full-immersion test with a unidirectional pressure-pulse-decay experiment. If analysis of a particular full immersion test performed on a given sample did not yield estimates having adequate accuracy, one could perform an axial experiment (for example, as depicted in Example 2) on the same sample under the same experimental conditions, and the data from both tests can be analyzed simultaneously. FIG. 14 provides a Monte Carlo analysis synthetic data modeling these two experiments on the same sample. It is assumed that both experiments have equal reservoir volumes ($\gamma_0=\gamma_1=\gamma/2$), and the first 1% of data are ignored to allow early-time phenomena to abate. Employing this approaching would result in parameter estimates within 5% of their true value under all the test conditions given, a marked improvement from the accuracies presented for a single full-immersion test as shown in FIG. 11. This, of course comes at the expense of an additional experiment, but one that completes approximately 8 times faster than a standard pressure-pulse decay.

Example 8—Analytical Models, Numerical Models and Parameter Estimation Procedures Various analytical models and procedures that may be used with the methods of the present disclosure are provided in this Example.

Numerical Approximation Scheme

Figure 15:
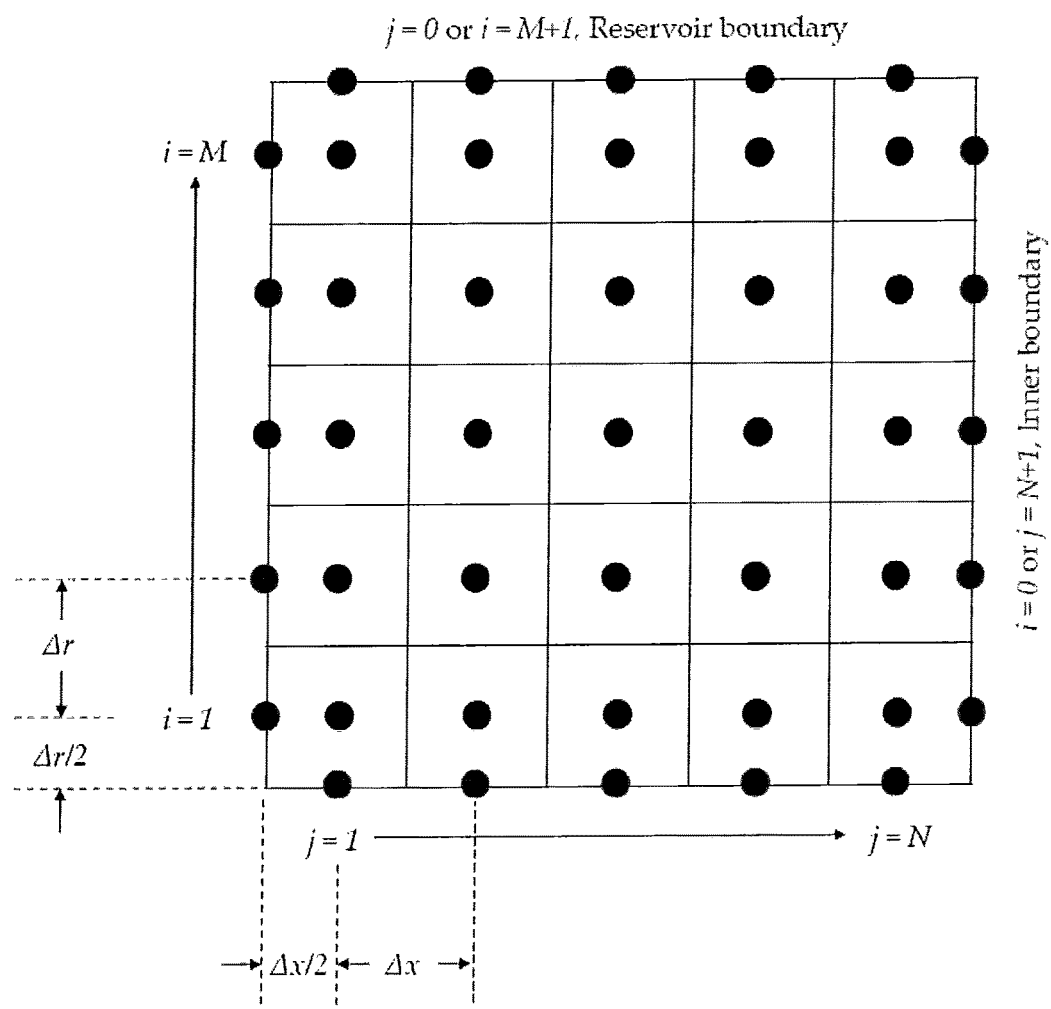
FIG. 15—shows an exemplary discretization scheme to approximate the solution to the full immersion pressure-pulse decay method.

FIG. 15 displays the discretization scheme employed to approximate the solution to the full immersion pressure-pulse-decay. The dependent variable is calculated at the center of each element, and the boundary values are calculated separately. The outer boundary (displayed in red) represents the value in the reservoir and is stored as a scalar value for each time step. The inner boundaries (horizontal boundary, $p_H$ shown in blue, vertical boundary, $p_V$ shown in green) are stored as separate arrays.

Spatial Discretization

A finite-difference numerical approximation scheme is employed to approximate the solution of Eq. 1, with initial and boundary conditions defined in Eqs. 4 to 6. The discretized form of the continuous function $p_D^*(r_D, x_D, t^*_{D,R})$ is reinterpreted as $p(r_i, x_j, t^k)$ or simply $p_{i,j}^k$. As a result the spatial derivatives of $p_D$ from Eq. 1, based on its Taylor series, can be approximated with the new notation using Eqs. B.1 to B.3. Note the custom finite-difference coefficients that were calculated at the boundaries of the inner domain.

$$\left(\frac{\partial p_D}{\partial r_D}\right)^k_{i,j} \approx \frac{p_{i+1,j}^k - p_{i-1,j}^k}{2\Delta r} + O(\Delta r^2); 1 < i < M, 1 \leq j \leq N$$

$$\left(\frac{\partial p_D}{\partial r_D}\right)^k_{i,j} \approx \frac{-4p_{0,j}^k + 3p_{1,j}^k + p_{2,j}^k}{3\Delta r} + O(\Delta r^2)$$

$$\left(\frac{\partial p_D}{\partial r_D}\right)^k_{M,j} \approx \frac{4p_{M+1}^k - 3p_{M,j}^k - p_{M-1,j}^k}{3\Delta r} + O(\Delta r^2) \quad (B.1)$$

$$\left(\frac{\partial^2 p_D}{\partial r_D^2}\right)^k_{i,j} \approx \frac{p_{i+1,j}^k - 2p_{i,j}^k + p_{i-1,j}^k}{\Delta r^2} + O(\Delta r^2); 1 < i < M, 1 \leq j \leq N$$

$$\left(\frac{\partial^2 p_D}{\partial r_D^2}\right)^k_{i,j} \approx \frac{3.2p_{0,j}^k - 5p_{1,j}^k + 2p_{2,j}^k - 0.2p_{3,j}^k}{\Delta r^2} + O(\Delta r^2)$$

$$\left(\frac{\partial^2 p_D}{\partial r_D^2}\right)^k_{M,j} \approx \frac{3.2p_{i,0}^k - 5p_{M,j}^k + 2p_{M-1,j}^k - 0.2p_{M-2,j}^k}{\Delta r^2} + O(\Delta r^2) \quad (B.2)$$

$$\left(\frac{\partial^2 p_D}{\partial x_D^2}\right)^k_{i,j} \approx \frac{p_{i,j+1}^k - 2p_{i,j}^k + p_{i,j-1}^k}{\Delta x^2} + O(\Delta x^2); 1 \leq i \leq M, 1 < j < N$$

$$\left(\frac{\partial^2 p_D}{\partial x_D^2}\right)^k_{i,1} \approx \frac{3.2p_{i,0}^k - 5p_{i,1}^k + 2p_{i,2}^k - 0.2p_{i,3}^k}{\Delta x^2} + O(\Delta x^2)$$

$$\left(\frac{\partial^2 p_D}{\partial x_D^2}\right)^k_{i,N} \approx \frac{3.2p_{i,N+1}^k - 5p_{i,N}^k + 2p_{i,N-1}^k - 0.2p_{i,N-2}^k}{\Delta x^2} + O(\Delta x^2) \quad (B.3)$$

Here i represents the radial index $$\left(r_D = \left(i - \frac{1}{2}\right)\Delta r, i = 1 \ldots M; r_1 = \frac{\Delta r}{2}, r_M = 1 - \frac{\Delta r}{2}\right),$$

and j represents the axial index $$\left(x_D = \left(j - \frac{1}{2}\right)\Delta x, j = 1 \ldots N; x_1 = \frac{\Delta x}{2}, x_N = 1 - \frac{\Delta x}{2}\right).$$

In Equations B.1 to B.3, the Taylor-series approximation is truncated to leave only terms on the order of $\Delta r^2$ and $\Delta x^2$ or below, so this scheme is also second order accurate in space. Using the derivative approximations above, the final form of the numerical approximation of Eq. 1 is given in Eq. B.4.

$$\left(\frac{\partial p_D^*}{\partial t_{D,R}^*}\right)^k_{i,j} = \frac{1}{\left(i - \frac{1}{2}\right)\Delta r}\left(\frac{\partial p_D^*}{\partial r_D}\right)^k + \left(\frac{\partial^2 p_D^*}{\partial r_D^2}\right)^k_{i,j} + \lambda_x^2 \left(\frac{\partial^2 p_D^*}{\partial x_D^2}\right)^k_{i,j} \quad (B.4)$$

In order to calculate the mass-balance boundary condition (Eq. 6) another set of discretized partial derivatives was calculated at the boundary of each domain. These are given below in Eqs. B.5 and B.6.

$$\left(\frac{\partial p_D^*}{\partial r_D}\right)_{M+1,j}^k \approx \frac{8p_{M+1,j}^k - 9p_{M,j}^k + p_{M-1,j}^k}{3\Delta r} + O(\Delta r^2) \quad \text{(B.5)}$$

$$\left(\frac{\partial p_D^*}{\partial x_D}\right)_{i,0}^k \approx \frac{-8p_{i,0}^k + 9p_{i,1}^k - p_{i,2}^k}{3\Delta x} + O(\Delta x^2) \quad \text{(B.6)}$$

The integral in Eq. 6 is approximated using a rectangle rule. As each value of the integrand is calculated at the center of the rectangle, this approximation also has second-order accuracy.

$$\frac{\gamma}{2}\left(\frac{\partial p_D^*}{\partial t_{D,R}^*}\right)_{M+1,j}^k = \lambda_x^2 \Delta r^2 \sum_{i=1}^{M}(i-1)\left(\frac{\partial p_D^*}{\partial x_D}\right)_{i,0}^k - \Delta x_D \sum_{j=1}^{N}\left(\frac{\partial p_D^*}{\partial r_D}\right)_{M+1,j}^k \quad \text{(B.7)}$$

The no-flux boundary imposed at the interior of the domain (Eq. 5) is approximated with the discretized partial derivatives defined in Eqs. B.8 and B.9.

$$\left(\frac{\partial p_D^*}{\partial r_D}\right)_{0,j}^k \approx \frac{-8p_{0,j}^k + 9p_{1,j}^k - p_{2,j}^k}{3\Delta r} + O(\Delta r^2) = 0 \quad \text{(B.8)}$$

$$\left(\frac{\partial p_D^*}{\partial x_D}\right)_{i,N+1}^k \approx \frac{8p_{i,N+1}^k - 9p_{i,N}^k + p_{i,N-1}^k}{3\Delta x} + O(\Delta x^2) = 0 \quad \text{(B.9)}$$

Runge-Kutta Temporal Discretization

The temporal partial derivatives in Eqs. 1 and 6 are approximated with a fourth order Runge-Kutta method, yielding a numerical scheme that has fifth-order accuracy in time. The coefficients calculated for each time step are given in Eqs. B.10 to B.13.

$$(K_1)_{i,j}^k = \left(\frac{\partial p_D^*}{\partial t_{D,R}^*}\right)_{i,j}^k \quad \text{(B.10)}$$

$$(K_2)_{i,j}^k = \left(\frac{\partial p_D^*}{\partial t_{D,R}^*}\right)_{i,j}^k \bigg|_{p_{i,j}^k \to p_{i,j}^k + \frac{\Delta t}{2}(K_1)_{i,j}^k} \quad \text{(B.11)}$$

$$(K_3)_{i,j}^k = \left(\frac{\partial p_D^*}{\partial t_{D,R}^*}\right)_{i,j}^k \bigg|_{p_{i,j}^k \to p_{i,j}^k + \frac{\Delta t}{2}(K_2)_{i,j}^k} \quad \text{(B.12)}$$

$$(K_4)_{i,j}^k = \left(\frac{\partial p_D^*}{\partial t_{D,R}^*}\right)_{i,j}^k \bigg|_{p_{i,j}^k \to p_{i,j}^k + \Delta t(K_3)_{i,j}^k} \quad \text{(B.13)}$$

Having these defined the output values for the inner domain and outer boundaries are calculated using Eqs. B.14 and 6, respectively.

$$p_{i,j}^{k+1} = p_{i,j}^k + \frac{(K_1)_{i,j}^k + 2(K_2)_{i,j}^k + 2(K_3)_{i,j}^k + (K_4)_{i,j}^k}{6}\Delta t + O(\Delta t^5) \quad \text{(B.14)}$$

The model inversion method used in all cases thus far works by minimization of errors between experiment and model output in a least-squares sense. The sections below provide descriptions of the algorithms that were investigated and ultimately chosen to estimate the parameters of interest by analysis of experimental data. An algorithm and source code is provided in the specific instances where the method was used. Lastly, the challenges of future inversion schemes—namely an investigation of parameter sensitivity and solution uniqueness in addition to the need for higher computing capacity—are discussed.

Nonlinear Least-Squares Estimators

An indicator of "closeness of fit" between model outputs and experimental data has many distinct quantifications. One of the most common is the least-squared error, which defines the accuracy of a model output based on the sum total of squared residual errors. Put in matrix notation, the residual error r can be calculated in terms of experimental data y (in terms of experimental inputs, x) and model output f (in terms of x and parameter array, β) using Eq. C.1.

$$\epsilon = y(x) - f(x;\beta) \quad \text{(C.1)}$$

The scalar sum of residual errors S can then be calculated with Eq. C.2.

$$S = \epsilon_i \sigma_{ij}^{-2} \epsilon_j = \epsilon^T \Omega^{-1} \epsilon \quad \text{(C.2)}$$

This sum is written in the Einstein summation convention of tensors, where repeated indices denote a summation over all values of that index. Note the existence of weighting factors $\sigma_{i,j}^{-2}$ and the covariance matrix $\Omega$. These factors weight each observation based on its importance to model outputs. They are often, but not necessarily [70], based on measurement error. For an ordinary least-squares estimator, one can substitute the identity matrix I for $\Omega$, or the Kroenecker delta $\delta_{ij}$ for $\sigma_{ij}^{-2}$. To optimize the fit between model and experiment, then, the quantity S must be minimized. The paragraphs below outline multiple strategies of minimization, the last of which is used to calculate parameters from the transient tests described in this report. Although one can find detailed derivations of these algorithms in the literature [49, 79-81], basic descriptions of these derivations are provided here to better explain the reasoning behind their implementation.

Scaled Sensitivity Coefficients and Log-Based Parameters

As discussed herein, there are multiple reasons it is advantageous to use scaled sensitivity coefficients (defined by Eq. 20) than standard sensitivity coefficients. First, it allows a more direct comparison of the influence each parameter provides to the model output. Secondly, it allows the parameters to be determined on a log scale, where large differences in magnitude between parameters (e.g., $k \sim \mathcal{O}(10^{-21} \text{ m}^2)$ vs. $p_p^* \sim \mathcal{O}(10^{12} \text{ Pa s}^{-1})$) can be mitigated. Such drastic disparities in magnitude often lead to numerical instabilities while computing parameter estimations.

Gauss-Newton Minimization for Nonlinear Systems

Given a set of model parameters β, the squared errors will be minimized if condition defined by Eq. C.3 is met.

$$\nabla_\beta S = \frac{\partial S}{\partial \log \beta_j} \equiv 0 \quad \text{(C.3)}$$

This assures that the sum of squared errors are minimized with respect to the β-space by determining the set of parameters β that set the gradient of S identically equal to the zero vector, 0. Put in terms of the Jacobian matrix X, whose elements $X_{ij}$ are defined in Eq. C.4, the condition in Eq. C.3 is re-written as Eq. C.5.

$$X \equiv \nabla_\beta f; X_{ij} \equiv \frac{\partial f_i}{\partial \log \beta_j}\bigg|_{\beta_j = \tilde{\beta}_j} \quad (C.4)$$

$$\frac{\partial S}{\partial \log \beta_j} = \frac{\partial \epsilon_i \sigma_{il}^{-2} \epsilon_l}{\partial \log \beta_k} = -2 X_{ji} \sigma_{ik}^{-2} \epsilon_k = 0; X^T \Omega^{-1} \epsilon \equiv 0 \quad (C.5)$$

For linear models, the components of $\beta$ can be independently de-coupled from Eq. C.5 and solved directly. Errors in non-linear systems are minimized by approximating the model as linear in close vicinity to a given set of parameters and iteratively updating f by way of Eq. C.6, where k indicates the iteration index and $\Delta \vec{\tilde{\beta}}$ is the tensor representation of the parameter-change array $\Delta \tilde{\beta}$.

$$f_i^{k+1} \approx f_i^k + X_{in}^k \Delta \vec{\tilde{\beta}}^k \quad (C.6)$$

Having done so, the minimizing condition Eq. C.5 can be written as Eq. C.7.

$$X^T \Omega^{-1} \epsilon = X_{ji} \sigma_{il}^{-2} \epsilon_l = X_{ji}^k \sigma_{il}^{-2} (y_l - f_l^{k+1}) \approx X_{ji}^k \sigma_{il}^{-2} (y_l - f_l^k - X_{in}^k \Delta \vec{\tilde{\beta}}^k) \approx X_{ji}^k \sigma_{il}^{-2} \epsilon_l^k - X_{ji}^k \sigma_{il}^{-2} X_{in}^k \Delta \vec{\tilde{\beta}}^k = 0 \quad (C.7)$$

Equation C.7 can then be written in terms of the matrix A and vector b defined in Eq. C.8, resulting in Eq. C.9.

$$A \equiv X^T \Omega^{-1} X; b \equiv X^T \Omega^{-1} \epsilon \quad (C.8)$$

$$A^k \Delta (\log \tilde{\beta})^k = b^k \quad (C.9)$$

An updated value for $\tilde{\beta}$ is then calculated by solving Eq. C.9 for $\Delta (\log \tilde{\beta})^k$, and applying the result to Eq. C.10.

$$(\log \tilde{\beta})^{k+1} = (\log \tilde{\beta})^k + \Delta (\log \tilde{\beta})^k \quad (C.10)$$

This process is repeated until changes of the parameter array converge to a sufficiently small magnitude. This method works well when an initial guess for the parameter array, $\tilde{\beta}^0$, lies sufficiently close to the true solution $\tilde{\beta}$. However, limitations of the approximation given in Eq. C.6 yield poor results with an initial guess far from the solution.

Method of Steepest Descents

This technique minimizes error by incrementally changing the value of $\tilde{\beta}$ in the opposite direction of the gradient $\nabla_\beta S$. Changing $\tilde{\beta}$ in this manner, and limiting it to a small magnitude $\epsilon$, can be done by following Eq. C.11.

$$\Delta (\log \tilde{\beta})^k = -\frac{\nabla_\beta S}{\|\nabla_\beta S\|} \epsilon \quad (C.11)$$

As opposed to the Gauss-Newton procedure, this technique performs well at locations farther from the solution. However as it approaches the solution the gradient $\nabla_\beta S$, by definition, approaches 0, so the rate of convergence decreases.

Levenberg-Marquardt Modification

In order to combine the benefits of each of the algorithms posed thus far, while avoiding their weaknesses, the Levenberg-Marquardt modification to the Gauss-Newton and Steepest-Descents methods begins with Eq. C.12.

$$(A^k + v^k I) \Delta (\log \tilde{\beta})^k = b^k \quad (C.12)$$

Marquardt provides a rigorous mathematical proof that, by satisfying Eq. C.12, the error S is minimized within all possible directions of $\Delta \tilde{\beta}$ within a sphere of radius $\|\Delta \tilde{\beta}\|$ [80]. Although that proof is not reproduced here, one notices by inspection that both the Gauss-Newton and Steepest-Descents algorithms are represented by different values of the damping parameter, v. As v approaches zero, Eq. C.12 simplifies to Eq. C.9. Conversely, Eq. C.12 approaches Eq. C.11 as v becomes sufficiently large to marginalize the influence of A.

One last modification to Eq. C.12 is in order to fully define the Levenberg-Marquardt technique. By scaling C.12 by the standard deviation of the partial derivatives $\partial f_i / \partial b_j$ [80], Eq. C.12 is modified to Eq. C.13.

$$(A^k + v^k \text{diag}(A^k)) \Delta (\log \tilde{\beta})^k = b^k \quad (C.13)$$

Here, diag (A) represents the diagonal elements of A. This transformation allows larger changes of the elements $\Delta \log \tilde{\beta}_j$ of those parameters whose influence on the model output is lower.

In order to fully take advantage of the Levenberg-Marquardt technique, one must judiciously choose appropriate values for $v^k$ at each iteration of convergence. It should be chosen in such a way that allows it to asymptotically approach zero as successive iterations converge toward the solution. An initial value for the damping parameter $v^0$ should be chosen sufficiently large to decrease S on the subsequent iteration. Marquart provides one example algorithm for doing so [80], although many strategies are used in practice.

REFERENCES

[1] A. I. Dicker and R. M. Smits. A practical approach for determining permeability from laboratory pressure-pulse decay measurements. In International Meeting on Petroleum Engineering, number SPE 17578, pages 285-290, Tianjin, China, November 1988. Society of Petroleum Engineers.

[2] P. A. Hsieh, J. V. Tracy, C. E. Neuzil, J. D. Bredehoeft, and S. E. Silliman. Transient laboratory method for determining the hydraulic properties of 'tight' rocks I. Theory. International Journal of Rock Mechanics and Mining Sciences & Geomechanics Abstracts, 18(5):245-252, October 1981.

[3] S. E. Haskett, G. M. Narahara, and S. A. Holditch. A method for simultaneous determination of permeability and porosity in low-permeability cores. SPE Formation Evaluation, 3(3):651-658, September 1988.

[4] D. L. Luel and J. B. Curtis. Development of laboratory and petrophysical techniques for evaluating shale reservoirs. Technical report, Gas Research Institute, Houston, Tex., April 1996.

[5] R. W. Spears, D. Dudus, A. Foulds, Q. Passey, S. Sinha, and W. L. Esch. Shale gas core analysis: strategies for normalizing between laboratories and a clear need for standard materials. In SPWLA 52nd Annual Logging Symposium, number SPWLA-2011-A, Colorado Springs, Colo., May 2011. Society of Petrophysicists and Well Log Analysts.

[6] S. S. Chhatre, E. M. Braun, S. Sinha, M. D. Determan, Q. R. Passey, T. E. Zirkle, A. C. Wood, J. A. Boros, D. W. Berry, S. A. Leonardi, and R. A. Kudva. Steady state permeability measurements of tight oil bearing rocks. In International Symposium of the Society of Core Analysts, number SCA2014-12, Avignon, France, September 2014. The Society of Core Analysts.

[7] X. Ning, J. Fan, S. A. Holditch, and W. J. Lee. The measurement of matrix and fracture properties in naturally fractured cores. In SPE Rocky Mountain Regional/

Low Permeability Reservoirs Symposium, number SPE 25898, Denver, Colo., April 1993. Society of Petroleum Engineers.

[8] Q. R. Passey, K. M. Bohacs, W. L. Esch, R. Klimentidis, and S. Sinha. From oil-prone source rock to gas producing shale reservoir—geologic and petrophysical characterization of unconventional shale-gas reservoirs. In CPS/SPE International Oil & Gas Conference and Exhibition, number SPE 131350, Beijing, China, June 2010. Society of Petroleum Engineers.

[9] C. Sondergeld, K. Newsham, and J. Comisky. Petrophysical considerations in evaluating and producing shale gas resources. In SPE Unconventional Gas Conference, number SPE 131768, Pittsburgh, Pa., February 2010. Society of Petroleum Engineers.

[10] J. Bear. The equation of motion of a homogeneous uid. In Dynamics of fluids in porous media, chapter 5, pages 119-194. Dover Publications, Inc., New York, N.Y., 1988.

[11] J. Kamath, R. E. Boyer, and F. M. Nakagawa. Characterization of core scale heterogeneities using laboratory pressure transients. SPE Formation Evaluation, 7(3):219-227, September 1992.

[12] J. Kim and J. Lee. Novel apparatus to measure the low-permeability and porosity in tight and shale gas reservoir. In The Twenty-third International Offshore and Polar Engineering, volume 9, pages 61-67, Anchorage, Ak., 2013. International Society of Offshore and Polar Engineers.

[49] S. Finsterle and P. Persoff. Determining permeability of tight rock samples using inverse modeling. Water Resources Research, 33(8):1803-1811, 1997.

[79] J. V. Beck and K. J. Arnold, Parameter Estimation In Engineering and Science. John Wiley & Sons, New York, N.Y., 1977.

[80] D. W. Marquardt, An algorithm for least-squares estimation of nonlinear parameters. Journal of the Society for Industrial and Applied Mathematics, 11(2):431-441, 1963.

[81] K. evenberg. A method for the solution of certain non-linear problems in least squares. The Quarterly of Applied Mathematics, 2:164-168, 1944.

What is claimed:

1. A method for simultaneously characterizing a radial permeability, axial permeability, and a porosity, of a sample whose geometry is easily defined, the method comprising the steps of:
   a. placing the sample in a sealed reservoir containing a permeant such that the entire outer surface of the sample is exposed to the permeant;
   b. equilibrating an internal pore pressure of the sample and a pressure of the reservoir to reach an equilibrated pressure $p_0$;
   c. applying a pressure pulse to the reservoir and the entire outer surface area of the sample, wherein the pressure pulse increases the pressure in the reservoir to a pressure greater than the equilibrated pressure $p_0$;
   d. obtaining data representative of a pressure decay over time in the reservoir after application of the pressure pulse;
   e. inputting an initial estimate for the radial permeability, the axial permeability and the porosity based on the data into a flow model to generate a model output;
   f. providing potential values of the radial permeability, the axial permeability and the porosity based on the data until the model output provides an acceptable fit to the data; and
   g. using the potential values of the radial permeability, the axial permeability, and the porosity, that provide an acceptable fit to the data as the values for the radial permeability, the axial permeability, and the porosity.

2. The method of claim 1, wherein the initial estimate of the radial permeability and the porosity is provided by fitting the data to a radial flow model.

3. The method of claim 1, wherein the initial estimate for the axial permeability is from 0.5% to 2% of the radial permeability.

4. The method of claim 1, wherein the model output includes uncertainty estimates for the radial permeability, the axial permeability and the porosity and the uncertainty estimate is used to determine if the model output provides the acceptable fit to the data.

5. The method of claim 1, wherein the sample is not a fractured sample or a crushed sample.

6. The method of claim 1, wherein the sample is a cylindrical sample.

7. The method of claim 1, wherein the sample is extracted perpendicularly to its native bedding plane.

8. The method of claim 1, wherein the sample is a core sample extracted perpendicularly to its native bedding plane.

9. The method of claim 1, wherein the permeant is a gas or a liquid.

10. The method of claim 1, wherein the permeant is water or brine.

11. The method of claim 1, wherein the permeant is $N_2$ or He.

12. The method of claim 1, wherein the applying the pressure pulse is instantaneous or substantially instantaneous.

13. The method of claim 1, wherein the pressure pulse is less than 20 percent of the equilibrated pressure $p_0$.

14. The method of claim 1, wherein the pressure pulse is from 5 percent to 10 percent of the equilibrated pressure $p_0$.

15. The method of claim 1, wherein the equilibrated pressure $p_0$ is greater than 1000 pounds per square inch (psi).

16. The method of claim 1, wherein the equilibrated pressure $p_0$ is from 250 psi to 2000 psi.

17. The method of claim 1, wherein data is obtained multiple times per second.

18. The method of claim 1 further comprising generating a pressure decay over time curve based on the data.

19. The method of claim 1, wherein the method is accomplished in less than 24 hours.

20. The method of claim 1 further comprising;
   a. obtaining under similar experimental conditions a second data set by applying the pressure pulse to the axial face or the radial surface of the sample;
   b. inputting a second initial estimate for the radial permeability or the axial permeability and the porosity into the flow model to generate a second model output;
   c. providing potential values of the radial permeability, the axial permeability and the porosity until the model output provides an acceptable fit to the data and providing potential values for the radial permeability or the axial permeability and the porosity until the second model output provides an acceptable fit to the second data;
   d. using the potential values of the radial permeability, the axial permeability, and the porosity, that provide an acceptable fit to the data and the second data as the values for the radial permeability, the axial permeability, and optionally the porosity.

21. The method of claim 1, wherein the second initial estimate for the radial permeability or the axial permeability and the porosity is obtained from the method of claim 1.

22. A method for simultaneously characterizing a radial permeability, axial permeability, and a porosity, of a cylindrical sample, the method comprising the steps of:
   a. placing the sample in a sealed reservoir containing a permeant such that the entire outer surface of the sample is exposed to the permeant;
   b. equilibrating an internal pore pressure of the sample and a pressure of the reservoir to reach an equilibrated pressure $p_0$;
   c. applying a pressure pulse to the reservoir and the entire outer surface area of the sample, wherein the pressure pulse increases the pressure in the reservoir to a pressure greater than the equilibrated pressure $p_0$;
   d. obtaining data representative of a pressure decay over time in the reservoir after application of the pressure pulse;
   e. inputting a series of potential values for each of a plurality of parameters based on the data into an expression to produce a model output until the model output provides an acceptable fit to the data;
   f. determining the value for each of the plurality of parameters using the potential values of each of the plurality of parameters that provide an acceptable fit between the model output and the data;
   g. determining the radial permeability, the axial permeability and the porosity from the values.

23. The method of claim 22, wherein the sample is not a fractured sample or a crushed sample.

24. The method of claim 22, wherein the sample is a cylindrical sample.

25. The method of claim 22, wherein the sample is extracted perpendicularly to its native bedding plane.

26. The method of claim 22, wherein the sample is a cylindrical core sample extracted perpendicularly to its native bedding plane.

27. The method of claim 22, wherein the permeant is a gas or a liquid.

28. The method of claim 22, wherein the permeant is water or brine.

29. The method of claim 22, wherein the permeant is $N_2$ or He.

30. The method of claim 22, wherein the applying the pressure pulse is instantaneous or substantially instantaneous.

31. The method of claim 22, wherein the pressure pulse is less than 20 percent of the equilibrated pressure $p_0$.

32. The method of claim 22, wherein the pressure pulse is from 5 percent to 10 percent of the equilibrated pressure $p_0$.

33. The method of claim 22, wherein the equilibrated pressure $p_0$ is greater than 1000 pounds per square inch (psi).

34. The method of claim 22, wherein the equilibrated pressure $p_0$ is from 250 psi to 2000 psi.

35. The method of claim 22, wherein data is obtained multiple times per second.

36. The method of claim 22, wherein the parameters are selected from the group consisting of $p_p^*$, $\gamma$, $\tau_R$ and $\lambda_x^2$.

37. The method of claim 22, wherein the expression is o governing flow equation.

38. The method of claim 37, wherein the governing flow equation is:

$$\frac{\partial p_D^*}{\partial t_{D,R}^*} = \frac{\mu c}{(\mu c)_{ref}} \frac{\partial p_D^*}{\partial t_{D,R}} = \frac{1}{r_D}\frac{\partial p_D^*}{\partial r_D} + \frac{\partial^2 p_D^*}{\partial r_D^2} + \lambda_x^2 \frac{\partial^2 p_D^*}{\partial x_D^2},$$

$$\text{wherein } \tau_R \equiv \frac{n(\mu c)_{ref} R^2}{k_r} \text{ and } \lambda_x^2 \equiv \frac{k_r}{k_r}\left(\frac{D}{L}\right)^2.$$

39. The method of claim 22 further comprising generating a pressure decay over time curve based on the data.

40. The method of claim 22, wherein the method is accomplished in less than 24 hours.

41. The method of claim 22, further comprising determining a second permeability in the radial direction or a second permeability in the axial direction of the sample, the method comprising the steps of:
   a. obtaining under similar experimental conditions a second data representative of a pressure decay over time in the reservoir after application of the pressure pulse;
   b. inputting the series of potential values based on the data and a series of second potential values based on the second data for each of the plurality of parameters into the expression to produce the model output and a second model output until the model output and second model output provides an acceptable fit to the data and the second data;
   c. determining a value for each of the plurality of parameters using the potential values and second potential values of each of the plurality of parameters that provide an acceptable fit between the model output and the data and the second model output and the second data; and
   d. determining the permeability in the radial direction, the permeability in the axial direction, and optionally the porosity, from the values.

42. The method of claim 41, wherein the method is performed if the parameter $\gamma$ estimated by the method of claim 23 is >!0 or $\lambda_x^2$ estimated by the method of claim 23 is <0.001 or >1.

* * * * *

UNITED STATES PATENT AND TRADEMARK OFFICE
CERTIFICATE OF CORRECTION

| | |
|---|---|
| PATENT NO. | : 10,302,543 B2 |
| APPLICATION NO. | : 15/570977 |
| DATED | : May 28, 2019 |
| INVENTOR(S) | : Michael J. Hannon, Jr. |

It is certified that error appears in the above-identified patent and that said Letters Patent is hereby corrected as shown below:

In the Specification

After the Cross-Reference to Related Applications, please add the following:
--GOVERNMENT SUPPORT CLAUSE
This invention was made with Government support under grant number DE-FE0002224 awarded by the U.S. Department of Energy. The Government has certain rights in the invention.--

Signed and Sealed this
Thirty-first Day of October, 2023

Katherine Kelly Vidal
*Director of the United States Patent and Trademark Office*